(12) United States Patent
Martin-Lomas et al.

(10) Patent No.: US 6,716,826 B2
(45) Date of Patent: Apr. 6, 2004

(54) COMPOUNDS AND THEIR USES

(75) Inventors: Manuel Martin-Lomas, Seville (ES); Thomas William Rademacher, Oxford (GB); Hugo Norberto Caro, London (GB); Irene Francois, Woking (GB)

(73) Assignee: Rodaris Pharmaceuticals Limited, Oxford (GB)

( * ) Notice: Subject to any disclaimer, the term of this patent is extended or adjusted under 35 U.S.C. 154(b) by 127 days.

(21) Appl. No.: 09/798,004

(22) Filed: Mar. 2, 2001

(65) Prior Publication Data

US 2001/0041677 A1 Nov. 15, 2001

Related U.S. Application Data

(60) Provisional application No. 60/203,598, filed on May 12, 2000.

(51) Int. Cl.$^7$ ................... A61K 31/715; A61K 31/70

(52) U.S. Cl. ............... 514/54; 514/25; 514/35; 514/53; 514/62; 514/866; 536/17.2

(58) Field of Search ............... 514/32, 25, 53, 514/62, 866, 54; 536/17.2

(56) References Cited

U.S. PATENT DOCUMENTS

| | | | |
|---|---|---|---|
| 5,268,272 A | 12/1993 | Mullner et al. | |
| 5,395,828 A | 3/1995 | Schiebler et al. | |
| 5,550,166 A | 8/1996 | Ostlund et al. | |
| 5,652,221 A | 7/1997 | Larner et al. | |
| 6,004,938 A | 12/1999 | Frick et al. | |
| 2001/0041677 A1 | * | 11/2001 | Martn-Lomas et al. |
| 2001/0051606 A1 | * | 12/2001 | Martin-Lomas et al. |
| 2001/0053767 A1 | * | 12/2001 | Martin-Lomas et al. |
| 2001/0056072 A1 | * | 12/2001 | Martin Lomas et al. |

FOREIGN PATENT DOCUMENTS

| | | |
|---|---|---|
| EP | 0 520 372 A1 | 12/1992 |
| EP | 0 559 064 A2 | 9/1993 |
| EP | 0 845 475 A1 | 6/1998 |
| JP | 63196596 | 8/1988 |
| JP | 03237101 | 10/1991 |
| JP | 04120089 | 4/1992 |
| JP | 06293790 | 10/1994 |
| WO | WO 96/14075 | 5/1996 |
| WO | WO 98/10791 | 3/1998 |
| WO | WO 98/11116 | 3/1998 |
| WO | WO 98/11117 | 3/1998 |
| WO | WO 98/11435 | 3/1998 |
| WO | WO 98/50049 | 11/1998 |
| WO | WO 99/06421 | 2/1999 |
| WO | WO 99/38516 | 8/1999 |
| WO | WO 00/15254 | 3/2000 |
| WO | WO 00/39141 | 7/2000 |

OTHER PUBLICATIONS

Murahata et al., Carbohydrate Research, vol. 235, pp. 95–114, 1992.*

Jaworek et al., Tetrahedron Letters, vol. 40, pp. 667–670, Jan. 1999.*

Fernandez De La Pradilla, R. et al., "Improved preparation of acetals of myo–inositol and its (±)–1–benzyl ether: conformational analysis of di–O–isopropylidene–myo–inositol derivatives"; Carbohydrate Research, 207: 249–257 (1990).

Bernabé, M. et al., "Chiral recognition of 1–O–allyl and 1–O–benzyl–D– and –L– myo–inositol by cyclomaltohexaose and –hepatose (α–and β–cyclodextrin)"; Carbohydrate Research, 208: 255–259 (1990).

Zapta, A. et al., "Novel Highly Regioselective O–Alkylation and O–Acylation of myo–Inositol"; J. Org. Chem., 56:444–447 (1991).

Jaramillo, C. et al., "Synthesis of 1D–1,2–anhydro–myo-inositol"; Carbohydrate Research, 209: 296–298 (1991).

Jaramillo, C. et al., "Approaches to the Synthesis of Glycosyl Phosphatidly Inositols. Enantioselective Synthesis of Optically Active chiro– and myo–Inositols."; Tetrahedron Letters, 32(22):2501–2504 (1991).

Vasella, A. et al., "194. Convenient Synthesis of 2–Azido–2–deoxy–aldoses by Diazo Transfer"; Helvetica Chimica Acta, 74: 2073–2077 (1991).

Aguiló, A. et al., "The Regioselective Synthesis of Enantiomerically Pure myo–Inositol Derivatives. Efficient Synthesis of myo–Inositol 1,4,5–trisphosphate."; Tetrahedron Letters, 33(3): 401–404 (1992).

Zapata, A. et al., "Building blocks for the synthesis of glycosyl–myo–inositols involved in the insulin intracellular signalling process"; Carbohydrate Research, 234: 93–106 (1992).

Caro, H. et al., "Syntheses and insulin–Like activity of phosphorylated galactose derivatives"; Carbohydrate Research 240: 119–131 (1993).

Singh, K. et al., "Synthesis of Oligosaccharides Structurally Related to E–Selectin Ligands"; J. Chem. Soc., Chem. Commun., 775–776 (1994).

Chiara, J.L. et al., "A Steroselective Route to Enantiomerically Pure myo–Inositol Derivatives Starting from D–Mannitol"; Tetrahedron Letters, 35(18):2969–2972 (1994).

(List continued on next page.)

*Primary Examiner*—James O. Wilson
(74) *Attorney, Agent, or Firm*—Dann Dorfman Herrell and Skillman, P.C.

(57) ABSTRACT

Compounds having a mimetic or antagonistic property of an inositol phosphoglycan, and the uses of these compounds are disclosed, together with the use, e.g. to treat a condition ameliorated by administration of an IPG second messenger or an IPG antagonist thereof. Preferred compounds of the invention are based on the substituted cyclitols, and in particular, the compounds are based on the 1,6 linkage of two or more sugar residues to a cyclitol.

18 Claims, 8 Drawing Sheets

OTHER PUBLICATIONS

Zapata, A. et al., "Synthesis and investigation of the possible insulin–like activity of 1D–4–O–and 1D–6–O–(2–amino–2–deoxy–α–D–glucopyranosyl)– myo–inositol 1–phosphate and 1D–6–O–(2–amino–2–deoxy–α–D– glucopyranosyl)– myo–inositol 1,2–(cyclic phosphate)"; Carbohydrate Research, 264:21–31 (1994).

Jaramillo, C. et al., "An Effective Strategy for the Synthesis of 6–O–(2–Amino–2–deoxy–α–D–glucopyranosyl)–D–chiro– and –D–myo–inositol 1–Phosphate Related to Putative Insulin Mimetics"; J. Org. Chem., 59:3135–3141 (1994).

Varela–Nieto, I. et al., "Cell Signalling by Inositol Phosphoglycans from Different Species"; Comp. Biochem. Physiol., 115B(2): 223–241 (1996).

Martin–Lomas, M. et al., "The solution conformation of glycosyl inositols related to inositolphosphoglycan (IPG) mediators"; Tetrahedron: Asymmetry, 11:37–51 (2000).

Baeschlin, D.K. et al., "1,2–Diacetals in Synthesis: Total Synthesis of a Glycosylphosphatidylinositol Anchor of *Trypanosoma brucei*"; Chem. Eur. J., 6(1): 172–186 (2000).

Frick, W. et al., "Structure–Activity Relationship of Synthetic Phosphoinositolglycans Mimicking Metabolic Insulin Action"; Biochemistry, 37(38):13421–13436 (1988).

Jaworek, C.H. et al., "Synthesis of an Inositol–Containing Trisaccharide Related to Insulin Signal Transduction"; Tetrahedron Letters, 40: 667–670 (1999).

Deeg, M.A. et al., "Inositol Glycan Phosphate Derived from Human Erythrocyte Acetylcholinesterase Glycolipid Anchor and Inositol Cyclic 1,2–Phosphate Antagonize Glucagon Activation of Glycogen Phosphorylase"; Diabetes, 42(9): 1318–1323 (1993).

Güther, M.L.S. et al., "Molecular species analysis and quantification of the glycosylphosphatidylinositol intermediate glycolipid C from *Trypanosome brucei*"; Mol Biochem. Parasitol., 77(2): 137–145 (1996).

Mayer, T.G. et al., "Glycosyl Phosphatidylinositol (GPI) Anchor Synthesis Based on Versatile Building Blocks— Total Synthesis of a GPI Anchor of Yeast"; Eur. J. Org. Chem. 1153–1165 (1999).

Müller, G. et al., "Phosphoinositolglycan–Peptides from Yeast Potently Induce Metabolic Insulin Actions in Isolated Rat Adipocytes, Cardiomyocytes, and Diaphragms"; Endocrinology, 138:3459–3475 (1997).

Baeschlin, D.K. et al., "Rapid Assembly of Oligosaccharides: Total Synthesis of a Glycosylphosphatidylinositol Anchor of *Trypanosoma brucei*"; Angew. Chem. Int. Ed., 37(24): 3423–3427 (1998).

Derappe, C. et al., "Characterization of a New Oligosaccharide Containing myo–Inositol Found in Pregnancy Urine"; Carbohydrate Research, 115: 221–229 (1983).

Angyal, S.J. et al., "Cyclitols. Part XXII. Synthesis of Some Mannosyl– and Mannosyl–mannosyl–myoinositols, and of Galacintol"; J. Chem. Soc. (C), 433–438 (1996).

Reddy, K.K. et al., "Insulin Second Messengers: Synthesis of 6–O–(2–Amino–2–deoxy–α–D–glucopyranosyl)–D– chiro–inositol–1–phosphate"; Tetrahedron Lets., 34(49): 7869–7872 (1993).

Plourde, R. et al., "Synthesis of a Potentially Insulin–Mimetic Phosphodisaccharide", Tetrahedron Lets., 31(19):2693–2696 (1990).

Stralfors, P., "Insulin second messengers"; Bioessays, 19: 327–335 (1997).

Field, M.C., "Is there evidence for phospho–oligosaccharides as insulin mediators?"; Glycobiology, 7: 161–168 (1997).

Jones, D.R. et al., "The role of glycosyl–phosphatidylinositol in signal transduction"; Int. J. Biochem. Cell Biol., 30: 313–326 (1998).

Mato J.M. et al., "Partial Stucture of an Insulin–Sensitive Glycophospholipid"; Biochem. Biophys. Res. Commun., 146: 764–770 (1987).

Larner, J., "Rat Liver Insulin Mediator Which Stimulates Pyruvate Dehydrogenase Phosphatase Contains Galactosamine and D–Chiroinositol"; Biochem. Biophys. Res. Commun., 151: 1416–1426 (1988).

Caro, H.N. et al., "Isolation and Partial Characterisation of Insulin–Mimetic Inositol Phosphoglycans from Human Liver"; Biochem. Mol. Med., 61: 214–228 (1997).

Gigg, R. et al., "Synthesis of Glycosylphosphatidylinositol Anchors"; in "Glycopeptides and Related Compounds"; Large & Warren, Eds., Marcel Dekker, New York, 327–392 (1997).

Corey, E.J. et al., "Protection of Hydroxyl Groups as Tert-Butyldimethylsilyl Derivatives"; J. Am. Chem. Soc., 94: 6190–6191 (1972).

Ley, S.V. et al., "Cyclohexane–1,2–diacetals (CDA): A New Protecting Group for Vicinal Diols in Carbohydrates"; Angew. Chem. Int. Ed. Engl., 33:2290–2292 (1994).

Kinzy, W. et al., "Synthese des Trisaccharids aus er 'Repeating Unit' des Kapselpolysaccharids von *Neisseria meningitidis* (Serogruppe L)"; Liebigs Ann. Chem., 1537–1545 (1985).

Schmidt, R.R. et al., "Anomeric–Oxygen Activation for Glycoside Synthesis: The Trichloroacetimidate Method"; Adv. Carbohydr. Chem. Biochem. 50: 21–123 (1994).

Rademacher, T.W. et al., "Inositolphosphoglycan second messengers"; Brazillian J. Med. Biol. Res., 27: 327–341 (1994).

Murakata, C. et al., "Stereoselective total synthesis of the glycosyl phosphatidylinositol (GPI) anchor or *Trypanosoma brucei*"; Carbohydrate Research, 235: 95–114 (1992).

Martin–Lomas, M. et al., "Inositolphosphoglycan Mediators Structurally Related to Glycosyl Phosphatidylinositol Anchors: Synthesis, Structure and Biological Activity"; Chem. Eur. J., 6(19): 3608–3621 (2000).

Ruda, K. et al., "Synthesis of an Inositol Phosphoglycan Fragment found in Leishmania Parasites"; Tetrahedron, 56(24): 3969–3975 (2000).

Dietrich, H. et al., "Glycosyl Inositol Derivatives Related to Inositolphosphoglycan Mediators: Synthesis, Structure, and Biological Activity"; Chem. Eur. J., 5(1): 320–336 (1999).

Smith, T.K. et al., "Parasite and mammalian GPI biosynthetic pathways can be distinguished using synthetic substrate analogues"; The EMBO Journal, 16(22): 6667–6675 (1997).

Fankhauser, C. et al., "Structures of Glycosylphosphatidylinositol Membrane Anchors from *Saccharomyces cerevisiae*"; J. Biol. Chem., 268(35): 26365–26374 (1993).

Menon, A.K. et al., "Cell–free Synthesis of Glycosyl–phosphatidylinositol Precursors for the Glycolipid Membrane Anchor of *Trypanosoma brucei* Variant Surface Glycoproteins"; J. Biol. Chem., 265(16): 9033–9042 (1990).

Sakata, K. et al., "2–O–(β–L–Arabinopyranosyl)–myo–inositol as a Main Constituent of Tea (*Camellia Sinensis*)"; Agric. Biol. Chem., 53(11): 2975–2979 (1989).

Gorin, P.A.J. et al., "Formation of O–β–D–Glucopyranosyl– and O–β–D–Galactopyranosyl–Myo–Inositols by Glycosyl Transfer"; Can. J. Chem., 43(8): 2259–2264 (1965).

Quemener, B. et al., "Ciceritol, A Pinitol Digalactoside from Seeds of Chickpea, Lentil and White Lupin", Phytochemistry, 22(8): 1745–1751 (1983).

Carter, H.E. et al., "Biochemistry of the Sphingolipids. XVII. Complete Structure of Tetrasaccharide Phytoglycolipid"; Biochemistry, 8(1): 383–388 (1969).

Wait, R. et al., "Strategies for the structure determination of parasite glycoconjugates using fast atom bombardment mass spectrometry"; Cienc. Cult. (Sao Paulo), 46(4): 255–261 (1994).

Previato, J.O. et al., "Structural Characterization of a Novel Class of Glycophosphosphingolipids from the Protozoan *Leptomonas samueli*"; J. Biol. Chem., 267(34): 24279–24286 (1992).

Hsieh, T.C.Y. et al., "Glycophosphoceramides from Plants—Purification and Characterization of a Novel Tetrasaccharide Derived from Tobacco Leaf Glycolipids"; J. Biol. Chem., 256(15): 7747–55 (1981).

Wait, R. et al., "Structure Determination of Phosphoinositol Oligosaccharides from Parasitic Protozoa Using Fast Atom Bombardment Mass Spectrometry"; Org. Mass Spectrom., 29(12): 767–781 (1994).

Smith, C.K. et al., "α–D–Mannopyranosyl–(1→4)–α–glucuronopyranosyl–(1→2)–myo–inositol, a new and unusual oligosaccharide from cultured rose cells"; Phytochemistry, 52: 387–396 (1999).

Ley, S.V. et al., "Microbial Oxidation in Synthesis: Preparation of a Potential Insulin Mimic from Benzene"; Synlett, 12: 997–998 (1992).

Crossman, Jr., A. et al., "Synthesis of some second generation substrate analogues of early intermediates in the biosynthetic pathway of glycosylphosphatidylinositol membrane anchors"; Carbohydrate Research, 321(1–2): 42–51 (1999).

Crossman, Jr. A. et al., "Parasite glyconconjugates. Part 7. Synthesis of further substrate analogues of early intermediates in the biosynthetic pathway of glycosylphosphatidylinositol membrane anchors"; J. Chem. Soc., Perkin Trans. 1: 2769–2774 (1997).

Smith, T.K. et al., "Substrate Specificity of the Dolichol Phosphate Mannose: Glucosaminyl Phosphatidylinositol α1–4–Mannosyltransferase of the Glycosylphosphatidylinositol Biosynthetic Pathway of African Trypanosomes"; J. Biol. Chem., 271(11): 6476–6482 (1996).

Cottaz, S. et al., "Parasite glycoconjugates. Part 3. Synthesis of substrate analogues of early intermediates in the biosynthetic pathway of glycosylphosphatidylinositol membrane anchors"; J. Chem. Soc. Perkin Trans. 1: 1673–1678 (1995).

Smith, T.K. et al., "Parasite–Specific Inhibition of the Glycosylphosphatidylinositol Biosynthetic Pathway by Stereoisometric Substrate Analogues"; Biochemistry, 39: 11801–11807 (2000).

Morris, J.C. et al., "Glycan Requirements of Glycosylphosphatidylinositol Phospholipase C from *Trypanosoma brucei*"; J. Biol. Chem., 270(6): 2517–2524 (1995).

Kunjara, S. et al., "Tissue Specific Release of Inositol Phosphoglycans"; Biopolymers and Bioproducts: Structure, Function and Applications, 301–306 (1995).

Khiar, N. et al., "Strategies for the Synthesis of Inositol Phosphoglycan Second Messengers"; Carbohydrate Mimics, Concepts and Methods, Chapleur Ed. Wiley VCH, 443–462 (1998).

* cited by examiner

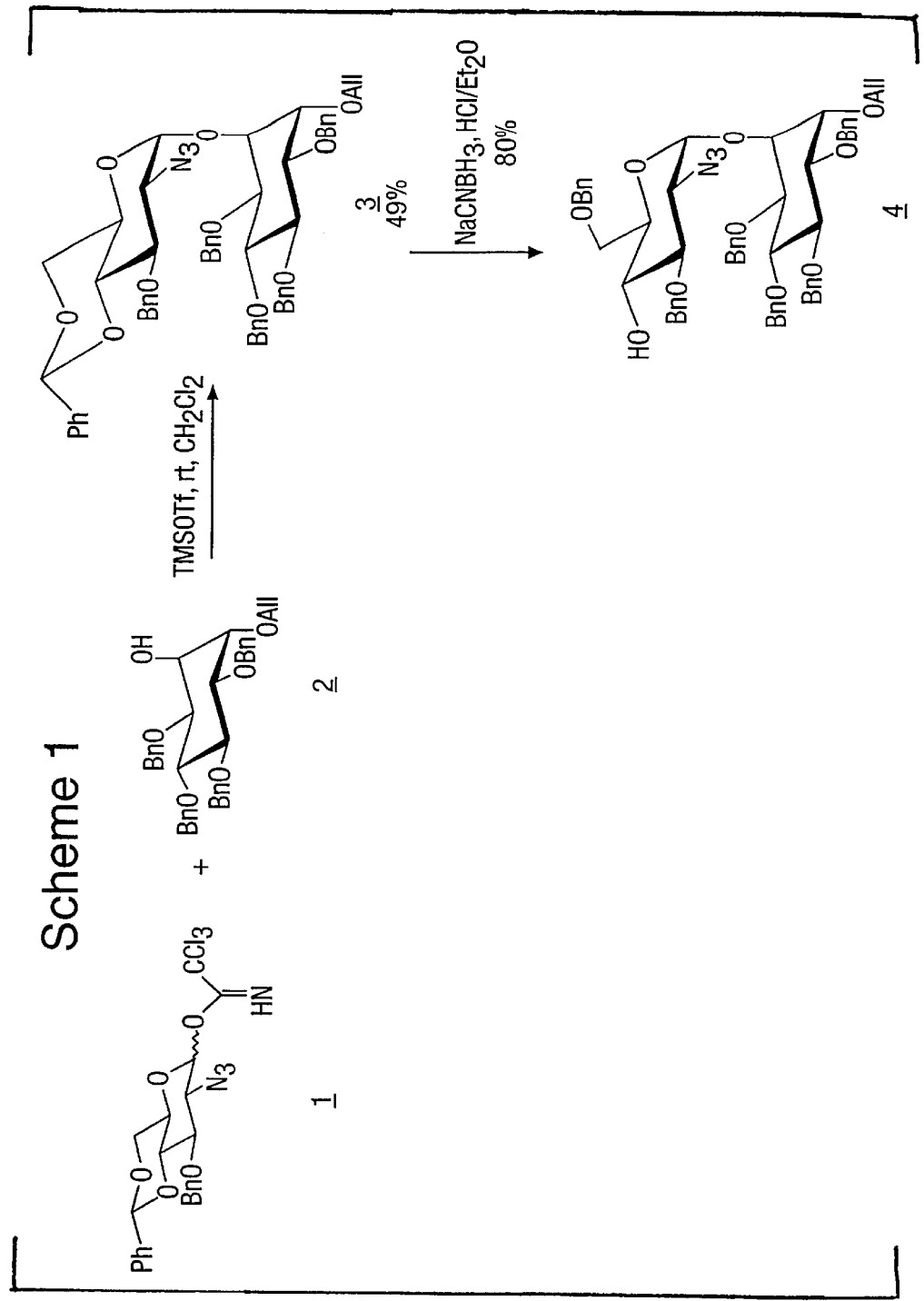

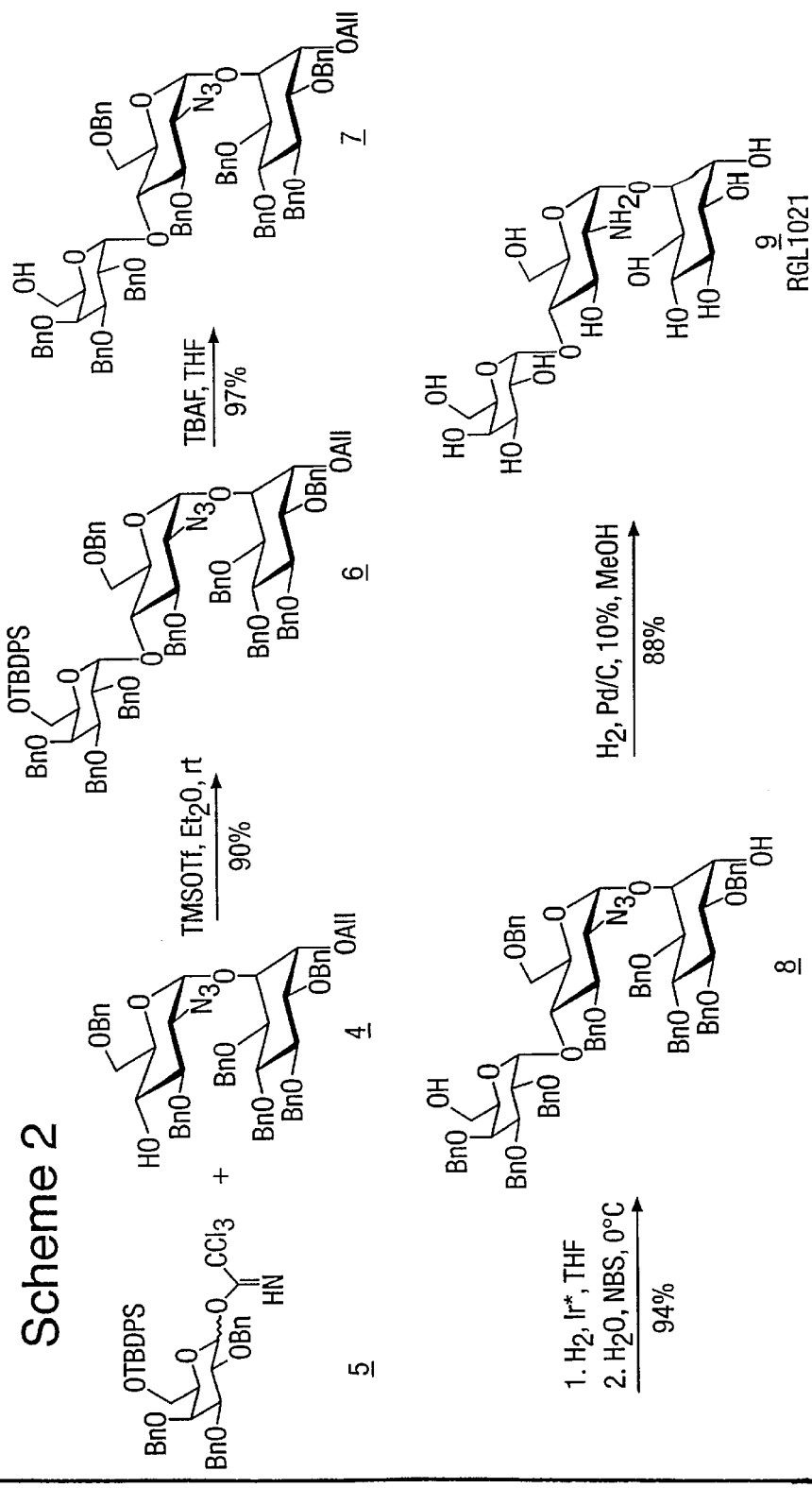

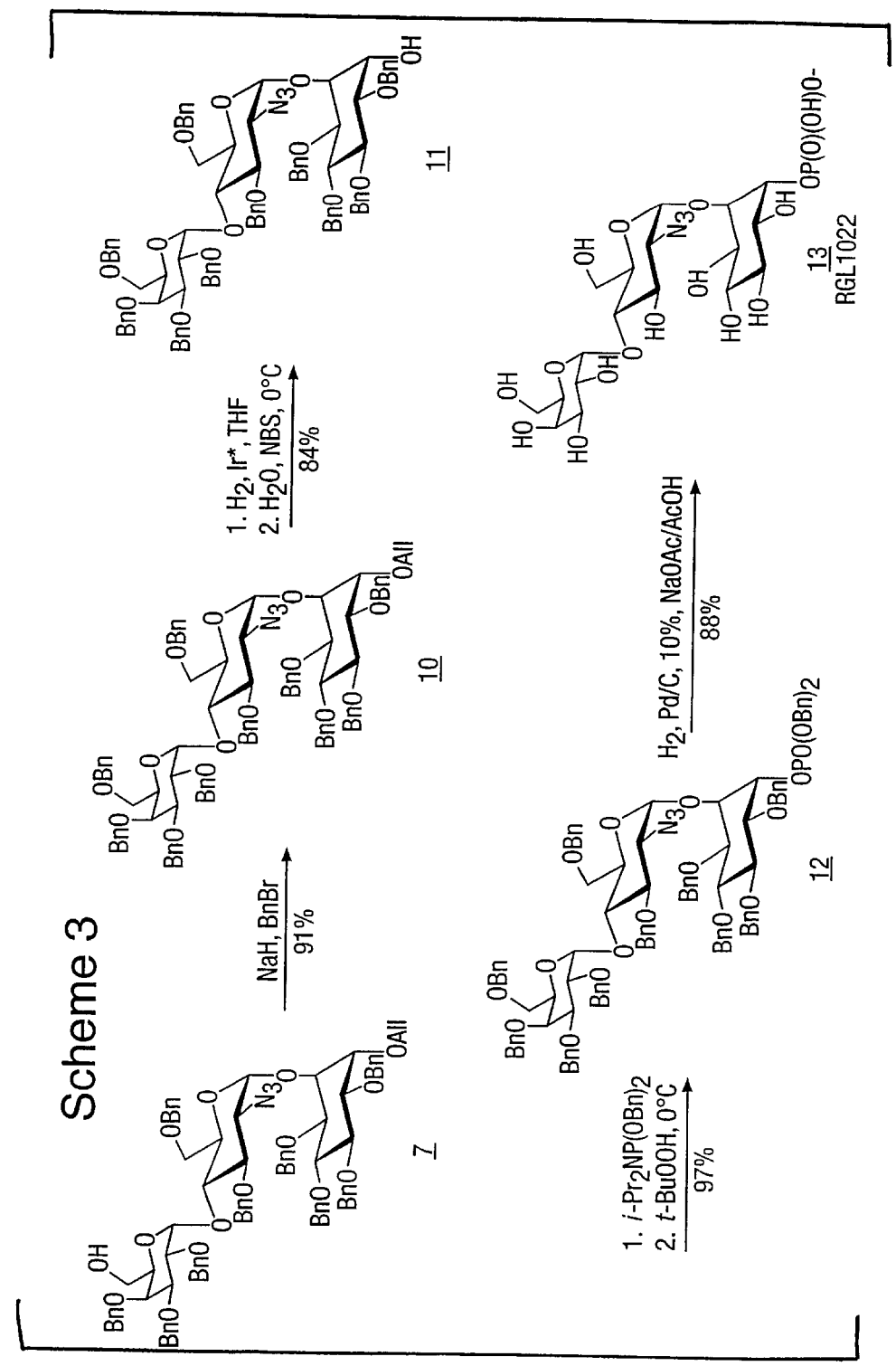

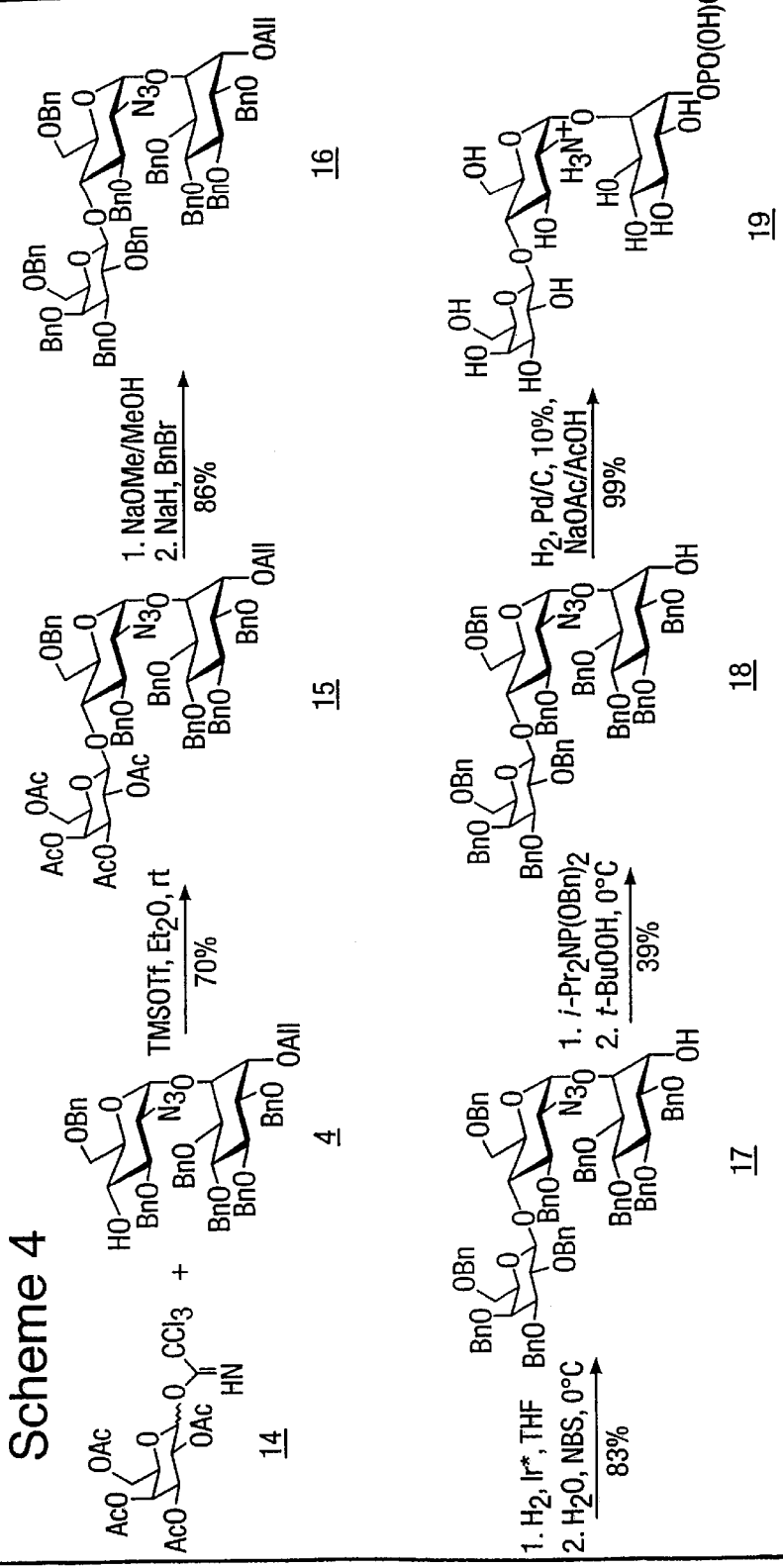
Scheme 4

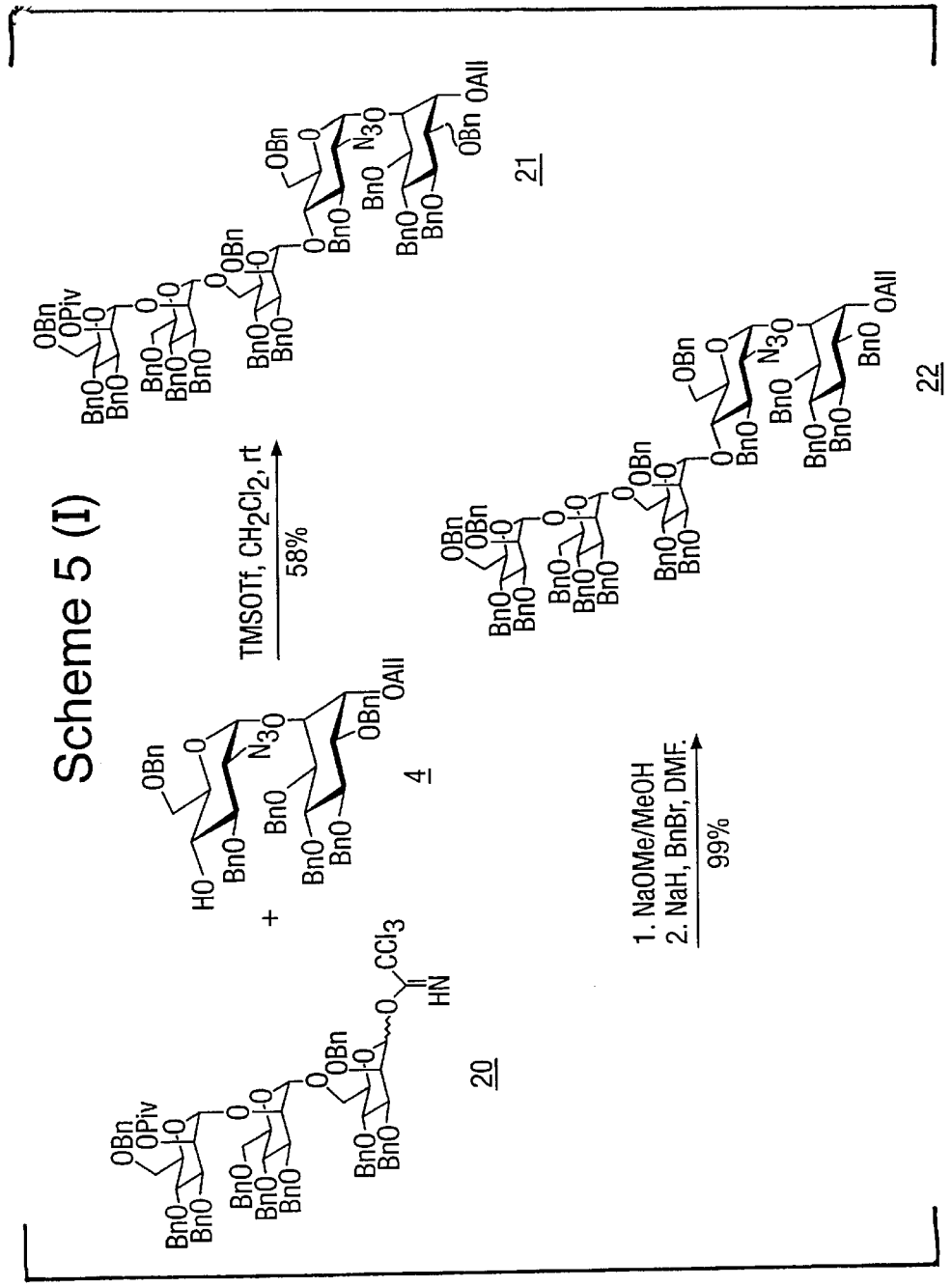
Scheme 5 (I)

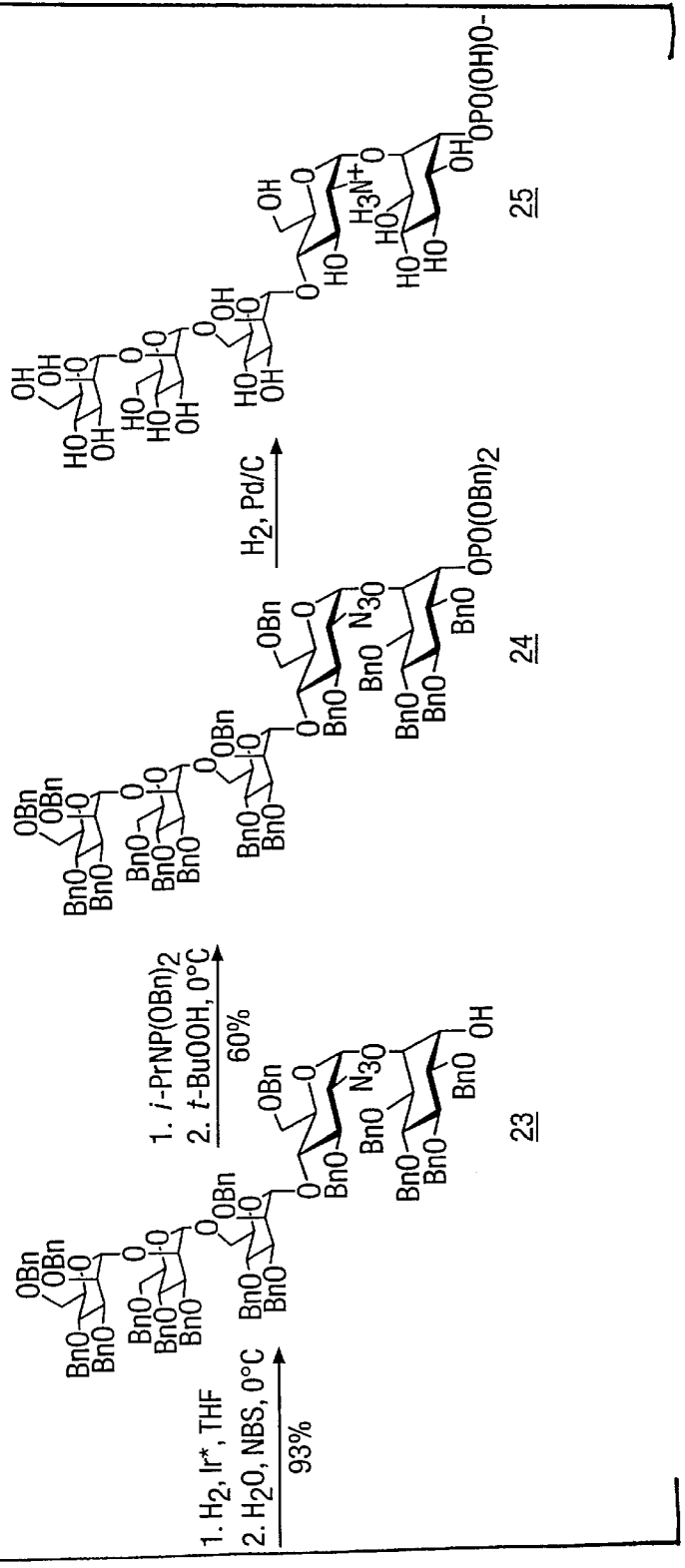

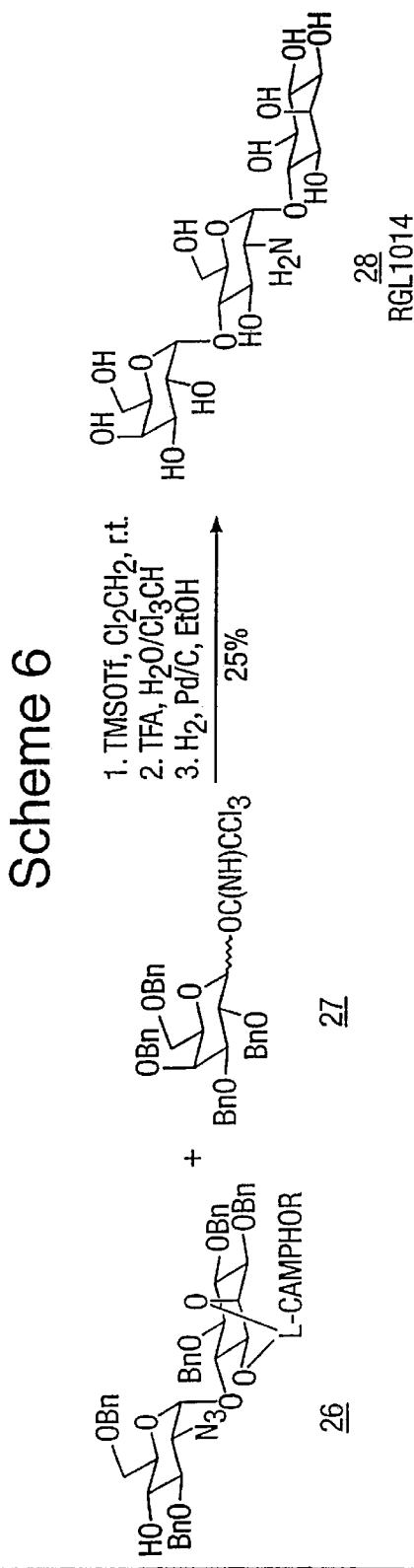

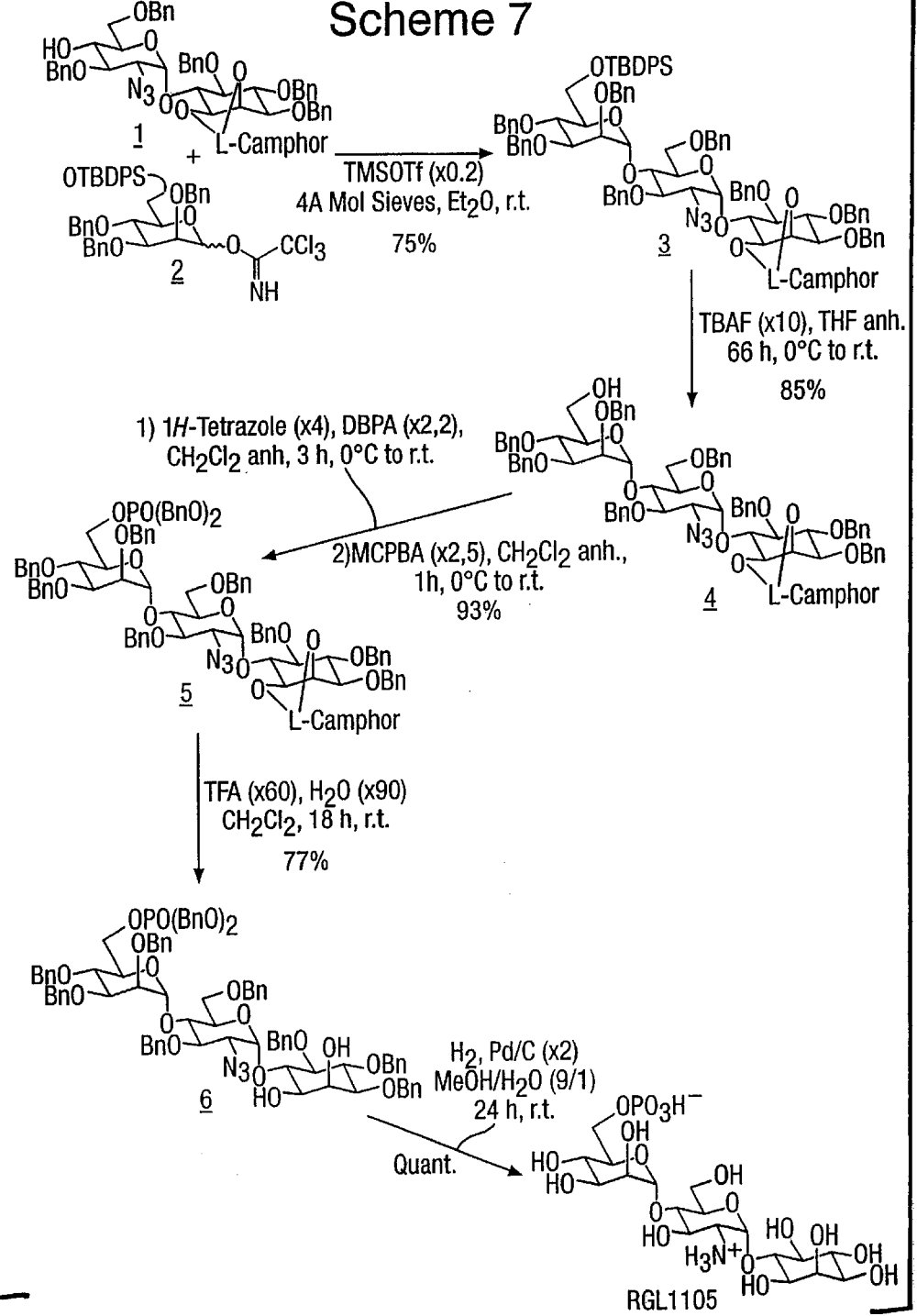

COMPOUNDS AND THEIR USES

CROSS REFERENCE TO RELATED APPLICATION(S)

This application claims the benefit of U.S. Provisional Application No. 60/203,598, filed May 12, 2000, the entire disclosure of which is incorporated by reference in this application.

FIELD OF THE INVENTION

The present invention relates to compounds and their uses, and in particular to compounds which have a mimetic or antagonistic property of an inositol phosphoglycan, and the uses of these compounds, e.g. to treat a condition ameliorated by administration of an IPG second messenger or an IPG antagonist thereof.

BACKGROUND OF THE INVENTION

Many of the actions of growth factors on cells are thought to be mediated by a family of inositol phosphoglycan (IPG) second messengers [13]. It is thought that the source of IPGs is a "free" form of glycosyl phosphatidylinositol (GPI) situated in cell membranes. IPGs are thought to be released by the action of phosphatidylinositol-specific phospholipases following binding of growth factors to receptors on the cell surface. There is evidence that IPGs mediate the action of a large number of growth factors including insulin, nerve growth factor, hepatocyte growth factor, insulin-like growth factor I (IGF-I), fibroblast growth factor, transforming growth factor β, the action of IL-2 on B-cells and T-cells, ACTH signalling of adrenocortical cells, IgE, FSH and hCG stimulation of granulosa cells, thyrotropin stimulation of thyroid cells, cell proliferation in the early developing ear and rat mammary gland.

Partially characterised inositolphosphoglycans (IPGs) have been postulated to mediate the action of a number of growth factors including insulin and insulin-like growth factor I (IGF-I) [1]. Despite their isolation from several tissues type, the precise chemical structures of these IPGs are, however, still unknown and two main structural groups have been proposed on the basis of the chemical composition [2,3] which display different biological activity and tissue distribution [4]; the family of glucosamine-myo-inositol containing IPGs (IPG-A) and the family of chiro-inositol-galactosamine containing IPcs (IPG-P).

In an attempt to establish the minimal structural requirements for biological activity, a number of compounds containing some of the basic structural motifs that have been postulated for IPG mediators have been synthesised in the art [5]. These synthetic compounds include O-(2-amino-2-deoxy-D-glucopyranosyl)-α(1→6)-chiro-inositol 1-phosphate and O-(2-amino-2-deoxy-D-glucopyranosyl)-α (1→6)-myo-inositol 1-phosphate [6].

U.S. Pat. No. 6,004,938 (Hoechst) discloses a group of synthetic inositol glycans having insulin-like action. The compounds are based on 2–6 monsaccharide units linked to an inositol moiety. The examples in the patent all employ myo-inositol and are composed of 5 or 6 units apart from two pseudo-trisaccharide compounds G and H. Compounds G and H are HO-PO(H)O-6Man-α(1→4)-GluN-α(1→6)-(L)inositol-1,2(cyclic) phosphate and HO-PO(H)O-6Man-α (1→4)-GluN-α(1→6)-(L)inositol, otherwise known as O-(6-hydrogenphosphonate-α-D-mannopyranosyl)-(1→4)-(2-ammonio-2-deoxy-α-D-glucopyranosyl)-(1→6)-L-myo-inositol-1,2-cyclic phosphate and O-(6-hydrogenphosphonate-α-D-mannopyranosyl)-(1→4)-(2-amino-2-deoxy-α-D-glucopyzanosyl)-L-myo-inositol. The properties of exemplified compounds are investigated in lipogenesis and glucose transport assays employing rat fat cells.

WO96/14075 (University of Virginia) discloses a generic family of compounds D-hexosamines linked to an inositol via a β1,4-linkage. The inositols can be myo or chiro-inositol or pinitol, while the hexosamines are glucosamine or galactosamine. However, this application describes the synthesis of just two compounds 4-O-(2-deoxy-2-amino-β-D-galactopyranosyl)-D-pinitol and 4-O-(2-deoxy-2-amino-β-D-galactopyranosyl)-D-chiro-inositol, or in JUPAC notation O-(2-amino-2-deoxy-β-D-galactopyranosyl)-(1→4)-D-pinitol and O-(2-amino-2-deoxy-β-D-galactopyranosyl)-(1→4)-D-chiro-inositol.

WO99/06421 (University of Virginia) describes synthetic insulin mimetic substances and includes a general formula I showing β1,4-linked disaccharides. However, despite this the compounds synthesised in this application are exactly the same as those disclosed in the applicant's earlier application, WO96/14075.

A multi-step synthesis of a IPG-P mimetic from glucose has been previously reported in Jaramillo et al [6], which discloses a compound called C4, 1-D-6-O-(2-amino-2-deoxy-α-D-glucopyranosyl)-chiro-inositol 1-phosphate. A further synthesis of C4 is described in our co-pending International Patent Application PCT/GB99/03715 (Rademacher Group Limited). Zapata et al [16] discloses three other compounds C1–C3 which are:

C1 1-D-4-O-(2-amino-2-deoxy-α-D-glucopyranosyl)-myo-inositol 1-phosphate.

C2 1-D-6-O-(2-amino-2-deoxy-α-D-glucopyranosyl)-myo-inositol 1-phosphate.

C3 1-D-6-O-(2-amino-2-deoxy-α-D-glucopyranosyl)-myo-inositol 1,2 cyclic-phosphate.

It remains a significant problem in the art to produce synthetic compounds which can mimic one or more of the activities of inositol phosphoglycans or which act as antagonists of IPGs.

SUMMARY OF THE INVENTION

Broadly, the present invention relates to IPG mimetic and antagonist compounds and to methods of producing the compounds and to their medical uses. The compounds disclosed herein are useful as synthetic mimetics of IPG-P or IPG-A second messengers and/or growth factors whose action is mediated by IPGs, or a competitive antagonists of IPGs. In particular, the compounds are based on the 1,6 linkage of two or more sugar residues to a cyclitol.

Accordingly, in a first aspect, the present invention provides a compound represented by the general formula:

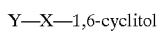

wherein:

X represents a sugar radical;

Y represents one to three sugar radicals;

the sugar radicals and cyclitol are individually unsubstituted or substituted with between one and four groups independently selected from:

(a) phosphoryl groups such as phosphate —O—P(O)(OH)$_2$; thiophosphate —O—P(S)(OH)$_2$; phosphate esters —O—P(O)(OR)$_2$; thiophosphate esters —O—P(S)(OR)$_2$; phosphonate —O—P(O)OHR;

thiophosphonate —O—P(S)OHR; substituted phosphonate —O—P(O)OR$_1$R$_2$; substituted thiophosphonate —O—P(S)OR$_1$R$_2$; —O—P(S)(OH)(SH); cyclic phosphate;
(b) other phosphorus containing compounds such as phosphoramidite —O—P(OR)-NR$_1$R$_2$ and phosphoramidate —O—P(O)(OR)-NR$_1$R$_2$;
(c) sulphur groups such as —O—S(O)(OH), —SH, —SR, —S(—O)—R, —S(O)$_2$R, RO—S(O)$_2^-$, —O—SO$_2$NH$_2$, —O—SO$_2$R$_1$R$_2$ or sulphamide —NHSO$_2$NH$_2$;
(d) amino groups such as —NHR, —NR$_1$R$_2$, —NHAc, —NHCOR, —NH—O—COR, —NHSO$_3^-$, —NHSO$_2$R, —N(SO$_2$R)$_2$, and/or amidino groups such as —NH—C(=NH)NH$_2$ and/or ureido groups such as —NH—CO—NR$_1$R$_2$ or thiouriedo groups such as —NH—C(S)—NH$_2$;
(e) hydroxy groups and substituted hydroxy groups such as —OR$_3$, where R$_3$ is C$_{1-10}$ unsubstituted or substituted alkyl, e.g. CHF$_2$ or CF$_3$, alkoxyalkyl, aryloxyalkyl, cycloalkyl, alkenyl (unsubstituted alkyl), alkylene (C$_{3-7}$ cycloalkyl), —OCOR, aryl, heteroaryl, acetal, or where two hydroxyl groups are joined as a ketal;
(f) halogen substituents such as fluorine or chlorine;
(g) hydrogen, e.g. to provide a deoxy sugar;
wherein R, R$_1$ and R$_2$ are independently hydrogen or C$_{1-10}$ unsubstituted or substituted alkyl or aryl;
with the proviso that the compound is not O-(6-hydrogenphosphonate-α-D-mannopyranosyl)-(1→4)-(2-ammonio-2-deoxy-α-D-glucopyraiosyl)-(1→6)-L-myo-inositol-1,2-cyclic phosphate and O-(6-hydrogenphosphonate-α-D-mannopyranosyl)-(1→4)-(2-amino-2-deoxy-α-D-glucopyranosyl)-L-myo-inositol.

In a further aspect the present invention provides a compound represented by the general formula:

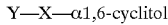

Y—X—α1,6-cyclitol wherein,
X represents a sugar radical;
Y represents one to three sugar radicals;
the sugar radicals and cyclitol are individually unsubstituted or substituted with between one and four groups independently selected from:
(a) phosphoryl groups such as phosphate —O—P(O)(OH)$_2$; thiophosphate —O—P(S)(OH)$_2$; phosphate esters —O—P(O)(OR)$_2$; thiophosphate esters —O—P(S)(OR)$_2$; phosphonate —O—P(O)OHR; thiophosphonate —O—P(S)OHR; substituted phosphonate —O—P(O)OR$_1$R$_2$; substituted thiophosphonate —O—P(S)OR$_1$R$_2$; —O—P(S)(OH)(SH); cyclic phosphate;
(b) other phosphorus containing compounds such as phosphoramidite —O—P(OR)—NR$_1$R$_2$ and phosphoramidate —O—P(O)(OR)—NR$_1$R$_2$;
(c) sulphur groups such as —O—S(O)(OH), —SH, —SR, —S(—O)—R, —S(O)$_2$R, RO—S(O)$_2^-$, —O—SO$_2$NH$_2$, —O—SO$_2$R$_1$R$_2$ or sulphamide —NHSO$_2$NH$_2$;
(d) amino groups such as —NHR, —NR$_1$R$_2$, —NHAc, —NHCOR, —NH—O—COR, —NHSO$_3^-$, —NHSO$_2$R, —N(SO$_2$R)$_2$, and/or amidino groups such as —NH—C(=NH)NH$_2$ and/or ureido groups such as —NH—CO—NR$_1$R$_2$ or thiouriedo groups such as —NH—C(S)—NH$_2$;
(e) hydroxy groups and substituted hydroxy groups such as —OR$_3$, where R$_3$ is C$_{1-10}$ unsubstituted or substituted alkyl, e.g. CHF$_2$ or CF$_3$, alkoxyalkyl, aryloxyalkyl, cycloalkyl, alkenyl (unsubstituted alkyl), alkylene (C$_{3-7}$ cycloalkyl), —OCOR, aryl, heteroaryl, acetal, or where two hydroxyl groups are joined as a ketal;
(f) halogen substituents such as fluorine or chlorine,
(g) hydrogen, e.g. to provide a deoxy sugar;
wherein R, R$_1$ and R$_2$ are independently hydrogen or C$_{1-10}$ unsubstituted or substituted alkyl or aryl;
with the proviso that the compound is not O-(6-hydrogenphosphonate-α-D-mannopyranosyl)-(1→4)-(2-ammonio-2-deoxy-α-D-glucopyranosyl)-(1→16)-L-myo-inositol-1,2-cyclic phosphate and O-(6-hydrogenphosphonate-α-D-mannopyranosyl)-(1→4)-(2-amino-2-deoxy-α-D-glucopyranosyl)-L-myo-inositol.

The compounds may be provided as racemic or diastereomeric mixtures, resolved or partially resolved optical isomers, and as pharmaceutically acceptable salts, esters and derivatives as discussed in more detail below.

Examples of compounds within this embodiment of the invention are RGL1014, RGL1021, RGL1022, RGL1105 and compounds 19 and 25.

Preferably, the X or Y sugar residue is a hexose or a pentose, and may be an aldose or a ketose. The sugar residue can a member of the D or L series and can include amino sugars, deoxy sugars and their uronic acid derivatives. Preferably, where the sugar residue is a hexose, it is selected from the group consisting of glucose, galactose or mannose, or substituted hexose sugar residues such as an amino sugar residue such as hexosamine, galactosamine or glucosamine, and more preferably D-glucosamine (2-amino-2-deoxy-D-glucose) or D-galactosamine (2-amino-2-deoxy-D-galactose). Preferred pentose sugar residues include arabinose, fucose and ribose. The X or Y sugar residue is optionally substituted at one, two, three or four positions, other than the anomeric position or the position of linkage of the other radical or to the cyclitol.

The cyclitol moiety is preferably selected from myo-inositol, chiro-inositol or pinitol (3-O-methyl-chiro-inositol), in either their D or L forms, and is optionally substituted at one or more of the positions other than the position of linkage to the sugar radical, or in the case of pinitol additionally the 3-position. The sugar radical is optionally substituted at one, two, three or four positions other than at the position of linkage to the inositol moiety (the anomeric position). Where the cyclitol moiety is substituted at the 3-position (e.g is a pinitol or a related compound), preferably the substituent is C$_{1-10}$ alkyl, and may be a substituted or unsubstituted primary, secondary or tertiary alkyl group. Examples of substituted groups include CF$_3$, X(CH$_2$)$_n$—O— (where X is hydrogen, or substituted or unsubstituted alkyl), CHF$_2$O—. A preferred alkyl group is methyl when the cyclitol is D or L-pinitol (3-O-methyl-chiro-inositol), and is optionally substituted at one or more of the positions other than the 3-position or the position of linkage to the sugar residue. In further embodiments, the cyclitol may have one or more of the hydroxyl groups through which the substituents described above are removed so that any substituent(s) are linked to the ring carbon atom. The sugar residue is optionally substituted at one, two, three, or four positions other than at the position of linkage to the inositol moiety.

Preferably the X and Y sugar residues are linked to each other via a 1,1 linkage, 1,2 linkage, 1,3 linkage, 1,4 linkage or 1,6 linkage. The linkage between the units may be an α or β linkage. The linkage of the X sugar residue to the cyclitol is generally a 1,6 linkage via one of the oxygen atoms of the cyclitol moiety. However, this oxygen atom can be replaced one or more times by —CH$_2$— or —S— groups.

In preferred embodiments, the present invention provides a compound, or a substituted form thereof as defined above, selected from the group consisting of:

RGL1014 O-(D-galactopyranosyl)-α(1,4)-O-(2'-amino-2'-deoxy-D-glucanopyranosyl)-α(1,6)-myo-inositol.
RGL1021 O-(D-galactopyranosyl)-α(1,4)-O-(2'-amino-2'-deoxy-D-glucanopyranosyl)-α(1,6)-chiro-inositol.
RGL1022 O-(D-galactopyranosyl)-α(1,4)-O-(2'-amino-2'-deoxy-D-glucanopyranosyl)-α(1,6)-chiro-inositol-1-phosphate.
RGL1105 1"-D-4'-O-(6"-phosphate-α-D-mannopyranosyl)-[1'-D-6-O-(2'-amino-2'-deoxy-α-D-glucopyranosyl)-myo-inositol].
Compound 25 O-α-D-Mannopyranosyl-(1-2)-O-α-D-mannopyranosyl-(1-6)-O-α-D-mannopyranosyl-(1-4)-O-2-ammonio-2-deoxy-α-D-glucopyranosyl-(1-6)-D-chiro-inositol-1-phosphate.
Compound 19 O-β-D-galactopyranosyl-(1-4)-2-ammonio-2-deoxy-α-D-galactopyranosyl-(1-6)-D-chiro-inositol-1-phosphate.

In a further aspect, the present invention provides methods for making the compounds of the invention or their intermediates as set out in the following experimental description and the schemes. In a further related aspect, the present invention further relates to compounds which are the novel intermediates described herein.

In a further aspect, the present invention provides one or more of the above compounds for use in a method of medical treatment. The compounds may be useful as IPG mimetics or IPG antagonists, e.g. competitive antagonists.

In a further aspect, the present invention provides the use of one or more of the above compounds for the preparation of a medicament for the treatment of a condition ameliorated by the administration of an inositol phosphoglycan (IPG) second messenger or an IPG antagonist. Examples of such conditions are set out in the pharmaceutical uses section below.

In a further aspect, the present invention provides a method of treating a condition in a mammal ameliorated by an inositol phosphoglycan (IPG) second messenger or an IPG antagonist, the method comprising administering to the mammal a therapeutically effective amount of one or more of the above compounds.

Embodiments of the invention will now be described by way of example and not limitation with reference to the accompanying drawings.

BRIEF DESCRIPTION OF THE FIGURES

Scheme 1 shows the synthesis of compound 4.

Scheme 2 shows the synthesis of RGL1021 from compound 4.

Scheme 3 shows the production of RGL1022 from compound 7.

Scheme 4 shows the production of compound 19, a derivative of compound 4.

Schemes 5(I) and 5(II) show the synthesis of compound 25.

Scheme 6 shows the preparation of trisaccharide 28 (RGL 1014).

Scheme 7 shows the preparation of compound RGL1105.

DETAILED DESCRIPTION

Inositol Phosphoglycans (IPGs)

IPG-A mediators modulate the activity of a number of insulin-dependent enzymes such as cAMP dependent protein kinase (inhibits), adenylate cyclase (inhibits) and cAMP phospho-diesterases (stimulates). In contrast, IPG-P mediators modulate the activity of insulin-dependent enzymes such as pyruvate dehydrogenase phosphatase (stimulates) and glycogen synthase phosphatase (stimulates). The A-type mediators mimic the lipogenic activity of insulin on adipocytes, whereas the P-type mediators mimic the glycogenic activity of insulin on muscle. Both A-and P-type mediators are mitogenic when added to fibroblasts in serum free media. The ability of the mediators to stimulate fibroblast proliferation is enhanced if the cells are transfected with the EGF-receptor. A-type mediators can stimulate cell proliferation in the chick cochleovestibular ganglia.

Soluble IPG fractions having A-type and P-type activity have been obtained from a variety of animal tissues including rat tissues (liver, kidney, muscle, brain, adipose, heart) and bovine liver. IPG-A and IPG-P biological activity has also been detected in human liver and placenta, malaria parasitized RBC and mycobacteria. The ability of an anti-inositolglycan antibody to inhibit insulin action on human placental cytotrophoblasts and BC3H1 myocytes or bovine-derived IPG action on rat diaphragm and chick cochleovestibular ganglia suggests cross-species conservation of many structural features. However, it is important to note that although the prior art includes these reports of IPG-A and IPG-P activity in some biological fractions, the purification or characterisation of the agents responsible for the activity is not disclosed.

IPG-A substances are cyclitol-containing carbohydrates, also containing Zn$^{2+}$ ions and phosphate and having the properties of regulating lipogenic activity and inhibiting cAMP dependent protein kinase. They may also inhibit adenylate cyclase, be mitogenic when added to EGF-transfected fibroblasts in serum free medium, and stimulate lipogenesis in adipocytes.

IPG-P substances are cyclitol-containing carbohydrates, also containing Mn$^{2+}$ and/or Zn$^{2+}$ ions and phosphate and having the properties of regulating glycogen metabolism and activating pyruvate dehydrogenase phosphatase. They may also stimulate the activity of glycogen synthase phosphatase, be mitogenic when added to fibroblasts in serum free medium, and stimulate pyruvate dehydrogenase phosphatase.

Methods for obtaining A-type and P-type mediators are set out in Caro et al, 1997, and in WO98/11116 and WO98/11117. Protocols for determining characteristic IPG biological activities such as PDH activation, PKA inhibition, acetylCoA activation, fructose-1,6-bis-phosphatase activity and lipogenesis are well known in the art, e.g. as described in Caro et al [1-4].

DRUG FORMULATION

The compounds of the invention may be derivatised in various ways. As used herein "derivatives" of the compounds includes salts, coordination complexes with metal ions such as Mn$^{2+}$ and Zn$^{2+}$, esters such as in vivo hydrolysable esters, free acids or bases, hydrates, prodrugs or lipids, coupling partners.

Salts of the compounds of the invention are preferably physiologically well tolerated and non toxic. Many examples of salts are known to those skilled in the art. Compounds having acidic groups, such as phosphates or sulfates, can form salts with alkaline or alkaline earth metals such as Na, K, Mg and Ca, and with organic amines such as triethylamine and Tris(2-hydroxyethyl)amine. Salts can be formed between compounds with basic groups, e.g. amines, with inorganic acids such as hydrochloric acid, phosphoric acid or sulfuric acid, or organic acids such as acetic acid, citric acid, benzoic acid, fumaric acid, or tartaric acid. Compounds having both acidic and basic groups can form internal salts.

Esters can be formed between hydroxyl or carboxylic acid groups present in the compound and an appropriate carboxylic acid or alcohol reaction partner, using techniques well known in the art.

Derivatives which as prodrugs of the compounds are convertible in vivo or in vitro into one of the parent compounds. Typically, at least one of the biological activities of compound will be reduced in the prodrug form of the compound, and can be activated by conversion of the prodrug to release the compound or a metabolite of it. An example of prodrugs are glycolipid derivatives in which one or more lipid moieties are provided as substituents on the sugar residue or the cyclitol moieties, leading to the release of the free form of the compound by cleavage with a phospholipase enzyme. Examples of prodrugs include the use of protecting groups which may be removed in situ releasing active compound or serve to inhibit clearance of the drug in vivo. Protecting groups are well known in the art and are discussed further below. An example of a suitable protecting group that might be used as a prodrug is the azido group used in the synthesis below, e.g. on the 2-position of the sugar moiety.

Other derivatives include coupling partners of the compounds in which the compounds is linked to a coupling partner, e.g. by being chemically coupled to the compound or physically associated with it. Examples of coupling partners include a label or reporter molecule, a supporting substrate, a carrier or transport molecule, an effector, a drug, an antibody or an inhibitor. Coupling partners can be covalently linked to compounds of the invention via an appropriate functional group on the compound such as a hydroxyl group, a carboxyl group or an amino group. Other derivatives include formuulating the compounds with liposomes.

Pharmaceutical Compositions

The compounds described herein or their derivatives can be formulated in pharmaceutical compositions, and administered to patients in a variety of forms, in particular to treat conditions which are ameliorated by the administration of inositol phosphoglycan second messengers or IPG antagonists such as competitive antagonist.

Pharmaceutical compositions for oral administration may be in tablet, capsule, powder or liquid form. A tablet may include a solid carrier such as gelatin or an adjuvant or an inert diluent. Liquid pharmaceutical compositions generally include a liquid carrier such as water, petroleum, animal or vegetable oils, mineral oil or synthetic oil. Physiological saline solution, or glycols such as ethylene glycol, propylene glycol or polyethylene glycol may be included. Such compositions and preparations generally contain at least 0.1 wt % of the compound.

Parental administration includes administration by the following routes: intravenous, cutaneous or subcutaneous, nasal, intramuscular, intraocular, transepithelial, intraperitoneal and topical (including dermal, ocular, rectal, nasal, inhalation and aerosol), and rectal systemic routes. For intravenous, cutaneous or subcutaneous injection, or injection at the site of affliction, the active ingredient will be in the form of a parenterally acceptable aqueous solution which is pyrogen-free and has suitable pH, isotonicity and stability.

Those of relevant skill in the art are well able to prepare suitable solutions using, for example, solutions of the compounds or a derivative thereof, e.g. in physiological saline, a dispersion prepared with glycerol, liquid polyethylene glycol or oils.

In addition to one or more of the compounds, optionally in combination with other active ingredient, the compositions can comprise one or more of a pharmaceutically acceptable excipient, carrier, buffer, stabiliser, isotonicizing agent, preservative or anti-oxidant or other materials well known to those skilled in the an. Such materials should be non-toxic and should not interfere with the efficacy of the active ingredient. The precise nature of the carrier or other material may depend on the route of administration, e.g. orally or parentally.

Liquid pharmaceutical compositions are typically formulated to have a pH between about 3.0 and 9.0, more preferably between about 4.5 and 8.5 and still more preferably between about 5.0 and 8.0. The pH of a composition can be maintained by the use of a buffer such as acetate, citrate, phosphate, succinate, Tris or histidine, typically employed in the range from about 1 mM to 50 mM. The pH of compositions can otherwise be adjusted by using physiologically acceptable acids or bases.

Preservatives are generally included in pharmaceutical compositions to retard microbial growth, extending the shelf life of the compositions and allowing multiple use packaging. Examples of preservatives include phenol, meta-cresol, benzyl alcohol, para-hydroxybenzoic acid and its esters, methyl paraben, propyl paraben, benzalconium chloride and benzethonium chloride. Preservatives are typically employed in the range of about 0.1 to 1.0% (w/v).

Preferably, the pharmaceutically compositions are given to an individual in a "prophylactically effective amount" or a "therapeutically effective amount" (as the case may be, although prophylaxis may be considered therapy), this being sufficient to show benefit to the individual. Typically, this will be to cause a therapeutically useful activity providing benefit to the individual. The actual amount of the compounds administered, and rate and time-course of administration, will depend on the nature and severity of the condition being treated. Prescription of treatment, e.g decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980. By way of example, and the compositions are preferably administered to patients in dosages of between about 0.01 and 100 mg of active compound per kg of body weight, and more preferably between about 0.5 and 10 mg/kg of body weight.

The composition may further comprise one or more other pharmaceutically active agents, either further compounds of the invention, inositol phosphoglycans, growth factors such as insulin, NGF or other growth factors listed below, or other drugs, e.g. those in use for the treatment of diabetes or other conditions set out below.

Medical Uses

As set out above, IPGs are second messengers for a range of different growth factors, including insulin, nerve growth factor, hepatocyte growth factor, insulin-like growth factor I (IGF-I), fibroblast growth factor, transforming growth factor $\beta$, the action of IL-2 on B-cells and T-cells, ACTH signalling of adrenocortical cells, IgE, FSH and hCG stimulation of granulosa cells, thyrotropin stimulation of thyroid cells, cell proliferation in the early developing ear and rat mammary gland. Consequently, IPGs or their antagonists can be used in the treatment or amelioration of disorders mediated by the growth factors or to mimic specific growth factor biological activities.

Examples of conditions which can be treated using IPGs or IPG antagonists include, diabetes, obesity, pre-eclampsia, neurotrophic disorders, hepatic damage and adrenal atrophy. WO98/10791 discloses that pre-eclampsia is characterised by elevated levels of IPG-P and that it can be treated using an IPG-P antagonist. Compounds of the invention which are IPG-P antagonists, e.g. antagonists which compete with wild-type IPG-P but lack one or more of its activities, could be used in the treatment of pre-eclampsia.

The use of both IPG-P and IPG-A and IPG-A antagonists in the diagnosis and treatment of diabetes is disclosed in WO98/11435. This application discloses that in some forms of diabetes the ratio of P:A-type IPGs is imbalanced and can be corrected by administering a medicament containing an appropriate ratio of IPG-P, IPG-A or antagonist(s) thereof. In particular, it describes the treatment of obese type II diabetes (NIDDM) patients with a P-type IPG and/or an A-type IPG antagonist and the treatment of IDDM or lean type II diabetes (body mass index <27) with a mixture of P- and A-type IPGs, typically in a P:A ratio of about 6:1 for males and 4:1 for females. The compounds and compositions of the present invention can be employed in such types of treatment. More particularly, the compounds are likely to be of use in the treatment of various form of diabetes and diabetic complications including diabetes due to insulin resistance, insulin resistance in type I diabetes and brittle diabetes, obese or lean type II diabetes, and of conditions associated with insulin resistance or insulin underproduction, such as neurotrophic disorders or polycystic ovary syndrome, lipodystrophy, age-related memory loss, and post-ischaemic damage secondary to stroke or post-transplant complications.

The compounds of this invention are also likely to be of use in controlling neuron proliferation or neurite outgrowth, either in vitro or in vivo, e.g. acting as a nerve or neurite growth factor mimetic second messenger. They may thus have applications in the treatment and/or diagnosis of any condition related to neuron proliferation or neurite differentiation. WO99/38516 discloses that IPG-A and synthetic mimetics thereof cause neuron proliferation, mimicking the action of the growth factor IGF-I. In contrast, IPG-P and synthetic mimetics thereof such as compound C4 cause neurite outgrowth. The neurons may be central (brain and spinal cord) neurons, peripheral (sympathetic, parasympathetic, sensory and enteric) neurons, or motor neurons.

Treatments may involve the treatment of damage to nerve, spinal cord or central nervous system damage secondary to trauma, or autoimmune or metabolic damage, or post-ischaemic damage secondary to stroke or post-transplant complications, motor neuron disease, neurodegenerative disorders or neuropathy. Damage to the nervous system includes the results of trauma, stroke, surgery, infection (e.g. by viral agents), ischemia, metabolic disease, toxic agents, or a combination of these or similar causes. Motor neuron disease includes conditions involving spinal muscular atrophy, paralysis or amyotrophic lateral sclerosis. Neurodegenerative disorders include Parkinson's disease, Alzheimer's disease, epilepsy, multiple sclerosis, Huntingdon's chorea and Meniere's disease.

The compounds of the invention may also be usefull as hepatocyte growth factor mimetic second messengers, e.g. in the preparation of medicaments for the treatment of hepatic damage caused by infection, alcohol abuse, drug sensitivity, or autoimmunity. The compounds may also be useful as fibroblast growth factor mimetic second messengers or epidermal growth factor mimetic second messengers, e.g. in the preparation of medicaments for the promotion of wound healing following surgery or trauma or tissue damage induced by ischaemia or autoimmunity.

In other embodiments, the compounds of the invention may be useful as adrenal cell growth factor mimetic second messengers or ACTH mimetic second messengers in the preparation of a medicament for the treatment of disease states involving adrenal atrophy.

Methods of Making the Compounds

Based on the disclosure herein, the knowledge in the art and in references [3-11], the skilled person could couple sugar residues and cyclitols together, optionally with one or more substituents.

Useful guidance on the synthesis of the exemplified compounds and for introducing the substituents set out herein is provided by the papers by Gigg & Gigg, Khiar & Martin-Lomas [5] and Baeschlin et al [18] and the references cited therein, Phosphoryl groups such as phosphate, cyclic phosphate or substituted phosphate or cyclic phosphate can be substituted into the compounds of the invention by the phosphate or phosphoramidite method, Bannwath et al, *Helvetica Chemica Acta,* 70:175–186, 1987 and Yu & Fraser-Reid, *Tetrahedron Lett.,* 29:979–982, 1988.

Phosphate protecting groups can also be synthesized according to the methods disclosed in Hoeben-Weyl, Methods of Organic Chemistry, volume 12/1 or 12/2, Teilheimer, Synthetic Methods of Organic Chemistry, Vol 45. Protecting groups for the OH of sugars include menthoxycarbonyl (MntCO), acetal (in particular, two R groups may together represent a bridging acetal such as O-cyclohexylidene, O-isopropylidene or O-benzylidene), tert-butyldimethylsilyl (TBDMS), benzyl (Bn), tert-butyldiphenylsilyl (TBDPS). Many protecting groups suitable for use in the syntheses and reactions of saccharides are known and are well documented in standard reference works. The choice depends in part on the route by which the compound is synthesised and/or on the uses to which it is to be put, including the reactions which it is subsequently intended to undergo.

Bioactivity Assays

The compounds of the invention can be tested for one or more the characteristic IPGP and/or IPG-A activities mentioned above to determine whether they will be suitable for use a IPG mimetics or antagonists. Preferred assays measure the effect of the compounds on PDH phosphatase, PKA or lipogenesis. Protocols for these assays are provided in Caro et al [14].

EXAMPLES

General Methods

All reactions were carried out under an atmosphere of dry argon using oven-dried glassware and freshly distilled and dried solvents. THF and diethlyl ether were distilled from sodium benzophenone ketyl. Dichloromethane and acetonitrile were distilled from calcium hydride. TLC was performed on Silica gel $GF_{254}$ (Merck) with detection by charring with phosphomolibdic acid/EtOH. For flash chromatography, Silica Gel (Merck 230–400 mesh) was used. Columns were eluted with positive air pressure. Chromatographic eluents are given as volume to volume ratios (v/v). Routine NMR spectra were recorded with Bruker Avance DPX300 ($^1$H, 300 MHz), Bruker Avance DRX400 ($^1$H, 400 MHz), and Bruker Avance DRX500 ($^1$H, 500 MHz)

spectrometers. Chemical shifts are reported in ppm, and coupling constants are reported in Hz. Spectra were referenced to the residual proton or carbon signals of the solvent. High-resolution mass spectra were recorded on a Kratos MS-80RFA 241-MC apparatus. Optical rotations were determined with a Perkin-Elmer 341 polarimeter. Elemental analyses were performed using a Leco CHNS-932 apparatus. The organic extracts were dried over anhydrous sodium sulfate and concentrated in vacuo.

The synthesis of D-chiro-inositol containing IPG-like compounds bearing complex oligosaccharide structures was envisaged using the trichloroacetimidate derivative 1 as glycosyl donor.

Glycosylation of 1 with 2 afforded pseudodisaccharides 3 in 40% yield (Scheme 1). Selective reductive opening of the benzylidene acetals in 3 with $NaBH_3CN$—HCl afforded the partially protected derivative 4 in good yield. Thus, compound 4 was used as starting material for the synthesis of some trisaccharidic IPG-like structures as indicated in Schemes 2, 3 and 4. Condensation of 4 with glycosyl donor 5 in ether afforded compound 6 in excellent yield (Scheme 2). Removal of the tert-butyldimethylsilyl group in 6 gave compound 7 in quantitative yield. After deallylation compound 7 was converted into 8 and this into the final pseudotrisaccharide 9 by catalytic hydrogenation.

Benzylation of the pseudotrisaccharide intermediate 7 yielded 10 (Scheme 3) that was deallylated to give 11. Phosphorylation of 11 using the phosphoramidite procedure gave 12 that was then hydrogenated to be converted into the final pseudotrisaccharide 13 in good yield.

The synthetic approach giving rise to the corresponding IPG-like structure with a b configuration of the terminal D-galactopyranosyl unit is shown in Scheme 4. Treatment of glycosyl acceptor 4 with trichloroacetimidate 14 gave rise to the fully protected pseudotrisaccharide 15 in good yield. Zemplen deacetylation of 15 followed by conventional benzylation yielded 16 that was deallylated to give 17. Phosphorylation of 17 gave 18 which was transformed into 19 after catalytic hydrogenation.

The synthesis of pseudopentasaccharide 25 was carried out following the strategy indicated in Schemes 5(I) and 5(II). Condensation of the trisaccharide trichloroacetimidate 20 with acceptor 44 afforded the pseudopentasaccharide derivative 21 in reasonable yield. Removal of the pivaloyl group in 21 followed by conventional benzylation yielded compound 22 in quantitative yield. Deallylation of 22 (Scheme 5(II)) gave 23 phosphorylation of which yielded 24. Final catalytic hydrogenation of 24 gave rise to the pseudopentasaccharide 25.

1-O-(2-Azido-2-deoxy-3-O-benzyl-4,6-O-benzlidene-α-D-glucopyranosyl)-6-O-allyl-2,3,4,5-tetra-O-benzyl-D-chiro-inositol (3)

A mixture 1 (520 mg, 0.985 mmol) and 2 (382 mg, 0.657 mmol) was dissolved in anhydrous $CH_2Cl_2$ (6.6 mL) and treated with a solution (2.50 mL) of trimethylsilyl triflate (80 mL) in $CH_2Cl_2$ (2 mL). The mixture was stirred at room temperature for 1.5 h and then 100 mL of the above solution of TMSOTf was added. After an additional hour with stirring (174 mg, 0.328 mmol) in $CH_2Cl_2$ (1.5 mL) was added and stirring was continued for 2 h, The mixture was the treated with $Et_3N$, evaporated to dryness and the residue fractionated on column chromatography (Hexane 8: AcoEt 1) to yield 3 (130.5 mg, 49%). $^1$H NMR ($CDCl_3$, 500 MHz): d 7.47–7.21 (m, 30H, ArH), 5.79 (ddt, $J_1$=5.6 Hz, $J_2$=10.5 Hz, $J_3$=17.1 Hz, 1H, $OCH_2CH$=$CH_2$), 5.51 (s, 1H, CH benzyliden), 5.17 (dd, $J_1$=1.5 Hz, $J_2$=17.2 Hz, 1H, $OCH_2CH$=CHH), 5.13 (dd, $J_1$=1.5 Hz, $J_2$=10.4 Hz, 1H, $OCH_2CH$=CHH), 4.97–4.76 (m, 10H, AB System), 4.70 (d, J=3.8 Hz, 1H, $H_{1e}$), 4.25–4.17 (m, 2H, $H_{5e}$+OCHHCH=$CH_2$), 3.99 (t, $J_1$=9.4 Hz, 1H, $H_{3e}$), 3.97 (m, 1H, O—CH—H—CH=$CH_2$), 3.95 (m, 1H, $H_{6ecq}$), 3.97–3.74 (m, 6H, ChiroIns), 3.64 (t, $J_1$=9.3 Hz, 1H, $H_{3e}$), 3.56 (t, J=10.3 Hz, 1H, $H_{6eax}$), 3.49 (dd, $J_1$=3.7 Hz, $J_2$=9.8 Hz, 1H, $H_{2e}$).

1-O-(2-Azido-2-decoxy-3,6-di-O-benzyl-α-D-glucopyranosyl)-6-O-allyl-2,3,4,5-tetra-O-benzyl-D-chiro-inositol (4)

To a solution of 3 (716 mg, 0.757 mmol) in THF (19 mL) 4 Å molecular sieves were added and the mixture stirred for 30 min. Then a 1M solution of sodium cyanoborohydride in THF (15 mL, 15.14 mmol) and a 1M solution of HCl in ether was added until the evolution of gas ceased. The mixture was then treated with saturated aqueous solution of $NaHCO_3$ and the organic layer washed with saturated NaCl, dried over $Na_2SO_4$ and evaporated. The residue was purified by column chromatography (Hexane 4: AcoEt 1) to give 4 (575 mg, 80%). $^1$H NMR ($CDCl_3$, 500 MHz): d 7.44–7.23 (m, 30H, Ar—H), 5.82 (ddt, $J_1$=5.6 Hz, $J_2$10.4 Hz, $J_3$=17.2 Hz, 1H, $OCH_2CH$=$CH_2$), 5.21 (broad dd, $J_1$=1.6 Hz, $J_2$=17.2 Hz, 1H, $OCH_2CH$=CHH), 5.16 (broad dd, $J_1$=1.6 Hz, $J_2$=10.4 Hz, 1H, $OCH_2CH$=CHH), 4.96–4.65 (m, 10H, AB System), 4.74 (d, J=3.6 Hz, 1H, $H_{1e}$), 4.44 (d, J=12.0 Hz, 1H, AB System), 4.32 (d, J=12.1 Hz, 1H, AB System), 4.22 (broad, dd, $J_1$=5.4 Hz, $J_2$=13.0 Hz, 1H, OCHHCH=$CH_2$), 4.12 (m, 1H, $H_{5e}$), 4.0 (m, 1H, OCHHCH=$CH_2$), 4.04–3.78 (m, 6H, ChiroIns), 3.76 (m, $2H_{3e}$++$H_{4e}$), 3.45 (dd, $J_1$=3.6 Hz, $J_2$=10.0 Hz, 1H, $H_{2e}$), 3.38 (dd, $J_1$=3.5 Hz, $J_2$=10.4 Hz, 1H, $H_{6eb}$), 3.27(dd, $J_1$=4.2 Hz, $J_2$=10.4 Hz, 1H, $H_{6ea}$), 2.39 (d, J=1.6 Hz, 1H, $OH_{4e}$).

O-(2,3,4-Tri-O-benzyl-6-O-tert-butyl diphenylsilyl-α-D-galactopyranosyl)-(1-4)-O-(2-azido-3,6-di-O-benzyl-2-deoxy-α-D-glucopyranosyl)-(1-6)-1-O-allyl-2,3,4,5-tetra-O-benzyl-D-chiro-inositol (6)

To a solution of 4 (144 mg, 0.152 mmol) and 5 (253 mg, 0.304 mmol) in ether (3 mL) 4 Å molecular sieves was added and the mixture stirred at room temperature for 15 min. Then a solution (98 mL) of TMSOTf in ether (40 mL in 2 mL) was added and the mixture stirred at room temperature. After 1 h 5 (85 mg) in ether (1 mL) was added. After 1 h, $Et_3N$ was added and the mixture was filtered, evaporated to dryness and the residue was purified by column chromatography (hexane 8: AcoEt 1) to give 6 (201, 3 mg, 82%). $^1$H NMR ($CDCl_3$, 500 MHz): d 7.60–7.08 (m, 55H, ArH), 5.79 (m, 1H, $OCH_2CH$=$CH_2$), 5.50 (d, J=3.6 Hz, $H_{1c}$), 5.17 (m, 1H, $OCH_2CH$=CHH), 5.12 (m, 1H, $OCH_2CH$=CHH), 4.97–4.48 (m, 16H, AB System), 4.75 (d, J=3.7 Hz, $H_{1b}$), 4.32 (d, J=12.1 Hz, 1H, AB System), 4.23–4.16 (m, 3H, AB System+$H_{5b}$+OCHHCH=$CH_2$), 4.05 (t, J=3.7 Hz, 1H), 4.01–3.78 (m, 12H, OCHHCH=$CH_2$+$H_{4b}$+$H_{3b}$+$H_{2c}$+$H_{3c}$+7H), 3.73–3.64 (m, 2H), 3.52 (dd, $J_1$4.1 Hz, $J_2$=10.7 Hz, 1H, $H_{6b}$), 3.45–3.41 (m, 2H, $H_{6b}$+$H_{2b}$), 1.06 (s, 9H, $^t$BuSi).

O-(2,3,4-Tri-O-benzyl-α-D-galactopyranosyl)-(1-4)-O-(2-azido-3,6-di-O-benzyl-2-deoxy-α-D-glucopyranosyl)-(1-6)-1-O-allyl-2,3,4,5-tetra-O-benzyl-D-chiro-inositol (7)

To a solution of 6 (197.7 mg, 0.122 mmol), 1M solution of TBAF (0.190 mL) was added and the mixture was stirred at room temperature. After 3 h, the mixture was treated with ice and extracted with CH$_2$Cl$_2$. The organic layer was dried and evaporated and the residue was purified by column chromatography (Hexane 3: AcOEt 1® Hex 2: AcOEt 1) to give 7 (285 mg, 96%). $^1$H NMR (CDCl$_3$, 500 MHz): d 7.38–7.11 (m, 45H, ArH), 5.78 (m, 1H, OCH$_2$CH=CH$_2$), 5.52 (d, J=3.6 Hz, 1H, H$_{1c}$), 5.18 (m, 1H, OCH$_2$CH=CHH), 5.14 (m, 1H, OCH$_2$CH=CHH), 4.98–4.38 (m, 18H, AB System), 4.76 (d, J$_1$=4.20 Hz, 1H, H$_{1b}$), 4.19 (m, 1H, OCHHCH=CH$_2$), 4.14 (m, 1H, H$_{5b}$), 4.04–3.76 (m, 12H, 6 ChiroIns+H$_{4b}$+H$_{2c}$+H$_{3b}$+H$_{3c}$+H4$_c$+OCHHCH=CH$_2$), 3.62 (m, 2H, H$_{5c}$+H$_{6b}$), 3.52 (m, 1H, H$_{6c}$), 3.48 (dd, J$_1$=3.6 Hz, J$_2$=10.1 Hz, 1H, H$_{2b}$), 3.35 (m, 1H, H$_{6c}$), 3.29 (dd, J$_1$1.9 Hz, J$_2$=11.4 Hz, 1H, H$_{6b}$). $^{13}$C NMR (CDCl$_3$, 125 MHz): d 139.03, 139.00, 138.74, 138.69, 138.45, 138.23, 138.04, 134.85, 128.48, 128.46, 128.43, 128.38, 128.35, 128.33, 128.31, 128.29, 129.26, 127.96, 127.86, 127.77, 127.70, 127.63, 127.57, 127.55, 127.47, 127.44, 127.41, 127.27, 117.20, 97.99 (anomeric C), 97.16 (anomeric C), 81.94, 81.85, 80.49, 79.94, 78.91, 78.23, 76.13, 75.90, 75.76, 74.94, 74.65, 74.33, 74.22, 74.18, 73.81, 73.75, 73.59, 73.26, 73.00, 72.53, 71.52, 71.04, 68.39, 64.05, 62.20.

O-(2,3,4-Tri-O-benzyl-α-D-galactopyranosyl)-(1-4)-(2-azido-3,6-di-O-benzyl-2-deoxy-α-D-glucopyranosyl)-(1-6)-2,3,4,5-tetra-O-benzyl-D-chiro-inositol (8)

A solution of the iridium catalyst in anhydrous THF (5.9–10$^{-3}$ M solution, 166 mL) previously treated under a hydrogen atmosphere for 30 minutes was added over a solution of 7 (45 mg, 0.033 mmol) in anhydrous THF (0.33 ml). The mixture was stirred at room temperature for 1.5 h and then THF (1.9 mL), NBS (8.4 mg, 0.047 mmol) and water (116 mL) were added and the mixture was stirred for 5 min, treated with saturated aqueous NaHCO$_3$, and extracted with CH$_2$Cl$_2$. The organic layer was dried and evaporated and the residue was purified by column chromatography (Hexane 2: AcOEt 1) to give pure 8 (41.2 mg, 44%). $^1$H NMR (CDCl$_3$, 500 MHz): d 7.36–7.11 (m, 45H, ArH), 5.54 (d, J=3.6 Hz, 1H, H$_{1c}$), 5.01–4.38 (m, 18H, AB System), 4.85 (d, J=3.8 Hz, 1H, H$_{1b}$), 4.16–4.14 (m, 2H, H$_{5c}$+H$_{5b}$), 4.08–3.78 (m, 10H, ChiroIns×3+H$_{4b}$+H$_{2c}$+H$_{3b}$+H$_{4c}$+H$_{3c}$+2H$_{6c}$), 3.63 (broad t, J=6.3 Hz, 1H, H$_{2a}$), 3.56–3.47 (m, 3H, ChiroIns×1+H$_{6b}$+H$_{2b}$), 3.35 (m, 1H, H$_{1a}$), 3.21 (m, 1H, H$_{6b}$), 2.71 (s, 1H, OH$_{1a}$), 2.53 (broad s, 1H, OH$_{6c}$). $^{13}$C NMR (CDCl$_3$, 125 MHz): d 138.91, 138.84, 138.65, 138.45, 138.24, 138.11, 138.05, 128.52, 128.46, 128.43, 128.41, 128.37, 128.36, 128.33, 128.31, 128.29, 128.28, 128.26, 128.23, 128.15, 128.00, 127.97, 127.94, 127.92, 127.86, 127.79, 127.69, 127.66, 127.62, 127.54, 127.51, 127.44, 127.40, 127.35, 127.32, 127.27, 127.25, 127.24, 127.22, 97.93 (anomeric C), 97.33 (anomeric C), 81.76, 81.29, 80.45, 80.02, 78.95, 78.33, 76.14, 75.89, 75.72, 75.56, 74.65, 74.33, 74.04, 73.92, 73.75, 73.60, 73.25, 72.98, 72.91, 72.52, 72.10, 68.15, 67.32, 63.99, 62.19, 29.73, 29.56.

O-(α-D-galactopyranosyl)-(1-4)-(2-amino-2-deoxy-α-D-glucopyranosyl)-(1-6)-D-chiro-inositol (9, RGL 1021)

To a solution of 8 (28 mg, 0.021 mmol) in MeOH (4.7 mL), five drops of AcOH and 10% Pd/C (100 mg) were added. The mixture was stirred at roonm temperature under a hydrogen atmosphere for 2.5 h and then filtered over Celite, washed with methanol and evaporated to give pure 9 (RGL 1021) (9.3 mg, 88%). $^1$H NMR (D$_2$, 500 MHz): d 5.50 (broad s, 1H, H$_{1c}$), 5.36 (broad s, 1H, H$_{1b}$), 4.33–3.60 (m, 17H), 3.48 (broad d, J=9.0 Hz, H$_{2b}$).

O-(2,3,4,6-Tetra-O-benzyl-α-D-galactopyranosyl)-(1-4)-(2-azido-3,6-di-O-benzyl-2-deoxy-α-D-glucopyranosyl)-(1-6)-1-O-allyl-2,3,4,5-tetra-O-benzyl-D-chiro-inositol (10)

Compound 7 (90.6 mg, 0.066 mmol) in DMF (1.3 mL) was treated with sodium hydride (5.25 mg, 0.131 mmol) and benzyl bromide (11.71 mL, 0.098 mmol) at room temperature for 1.5 h. The reaction mixture was cooled to 0° C., methanol was added and the mixture was extracted with CH$_2$Cl$_2$. The extract was washed with saturated aqueous ammonium chloride and then saturated aqueous sodium chloride, dried over Na$_2$SO$_4$, evaporated and purified by column chromatography (Hexane 5: AcOEt 1-Hex 2: AcOEt 1) to give pure 10 (87.5 mg, 91%) as a syrup. $^1$H NMR (CDCl$_3$, 500 MHz): d 7.40–7.10 (m, 50 H, ArH), 5.79 (m, 1H, OCH$_2$CH=CH$_2$), 5.52 (d, J=3.7 Hz, 1H, H$_{1c}$), 5.17 (m, 1H, OCH$_2$CH=CHH ), 5.13 (m, 1H, OCH$_2$CH=CHH), 5.00–4.62 (m, 14H, AB System), 4.77 (d, J=3.5 Hz, 1H, H$_{1b}$), 4.57–4.46 (m, 3H, AB System), 4.33 (d, J=12.3 Hz, 1H, AB System), 4.24 (d, J=11.9 Hz, 1H, AB System), 4.19 (d, J=11.9 Hz, 1H, AB System), 4.17 (m, 2H, H$_{5b}$+OCHHCH=CH$_2$), 4.06 (t, J=9.5 Hz, 1H, H$_{4b}$), 4.01 (m, 1H, H$_{2c}$), 3.95–3.87 (m, 5H, H$_{3b}$+H$_{4c}$+H$_{3c}$+H$_{5c}$+OCHHCH=CH$_2$), 4.2–3.75 (m, 6H, ChiroIns), 3.66 (dd, J=3.1 Hz, J$_2$=11.0 Hz, 1H, H$_{6b}$), 3.47 (m, 2H, H$_{2b}$+H$_{6c}$), 3.38 (d, J$_1$=5.5 Hz, J$_2$=8.5 Hz, 1H, H$_{6c}$), 3.34 (dd, J$_1$=1.6 Hz, J$_2$=10.8 Hz, 1H, H$_{6b}$). $^{13}$C NMR (CDCl$_3$, 125 MHz): d 138.78, 138.70, 138.61, 138.36, 138.32, 138.15, 137.97, 134.86, 128.36, 128.33, 128.32, 128.29, 128.27, 128.24, 128.22, 128.21, 128.19, 128.02, 127.95, 127.93, 127.91, 127.73, 127.71, 127.61, 127.57, 127.53, 127.48, 127.47, 127.45, 127.39, 127.33, 117.17, 98.40 (anomeric C), 96.98 (anomeric C), 81.94, 81.85, 80.48, 79.92, 78.94, 78.06, 77.31, 77.06, 76.80, 76.08, 75.83, 75.79, 74.83, 74.71, 74.55, 74.47, 74.24, 73.76, 73.70, 73.42, 73.30, 73.02, 72.87, 72.69, 72.49, 70.81, 69.88, 68.55, 64.05.

O-(2,3,4,6-Tetra-O-benzyl-α-D-galactopyranosyl)-(1-4)-(2-azido-3,6-di-O-benzyl-2-deoxy-α-D-glucopyranosyl-(1-6)-2,3,4,5 tetra-O-benzyl-D-chiro-inositol (11)

A solution of the iridium catalyst in anhydrous THF (5.9×10$^{-3}$ M solution, 300 mL) previously treated under a hydrogen atmosphere for 30 minutes was added over a solution of 10 (87 mg, 0.059 mmol) in anhydrous THF (0.6 mL). The mixture was stirred at room temperature for 1 h and then THF (3.4 ml), NBS (15.3 mg, 0.086 mmol) and water (208 mL) were added and the mixture was stirred again at room temperature for 10 min, treated with a saturated solution of NaHCO$_3$. The reaction mixture, was then extracted with CH$_2$Cl$_2$, washed with saturated NaCl dried over Na$_2$SO$_4$ and evaporated. The residue was purified by column chromatography (Hexane 3: AcoEt 1) to give pure 11 (70.8 mg, 84%). $^1$H NMR (CDCl$_3$, 500 MHz): d 7.40–7.12 (m, 50H, ArH), 5.55 (d, J=3.7 Hz, 1H, H$_{1c}$), 5.02–4.42 (m, 17H, AB System), 4.85 (d, J=3.7 Hz, 1M, H$_{1b}$), 4.31 (d, J=12.2 Hz, 1H, AB System), 4.25 (d, J=11.7 Hz, 1H, AB System), 4.20 (d, J=11.7 Hz, 1H, AB System), 4.19–4.15 (m, 2H, ChiroIns×1+H$_{5b}$), 4.08 (m, 1H, H$_{4b}$), 4.06 (m, 1H, H$_{1a}$), 4.03 (dd, J$_1$=3.7 Hz, J$_2$=10.2 Hz, H$_{2c}$), 3.98–3.86 (m, 7H, H$_{3c}$+H$_{5c}$+H$_{3b}$+H$_{6b}$+ChiroIns×3), 3.80 (t, J=9.2 Hz, 1H, H$_{4c}$), 3.60 (dd, J$_1$=3.2 Hz, J$_2$=11.0 Hz, 1H, ChiroIns), 3.50–3.47 (m, 2H, H$_{2b}$+ChiroIns), 3.39 (dd, J$_1$=5.5 Hz, J$_2$=8.6 Hz, H$_{6b}$), 3.28 (dd, J$_1$=1.8 Hz, J$_2$=11.0 Hz, 1H, ChiroIns). $^{13}$C NMR (CDCl$_3$, 125 MHz): d 138.95, 138.92, 138.75, 138.67, 138.62, 138.40, 138.35, 138.17, 138.16, 137.98, 137.52, 137.42, 137.40, 137.38, 137.36, 137.35, 137.34, 137.32, 137.31, 137.27, 137.25, 137.24, 137.22, 137.21, 137.17, 137.13, 137.11, 137.09, 137.01, 127.99, 127.95, 127.92, 127.73, 127.72, 127.63, 127.55, 127.53, 127.49, 127.48, 127.44, 127.40, 127.38, 127.37, 127.33, 98.30 (anomeric C), 97.25 (anomeric C), 81.76, 81.30, 80.44, 80.04, 78.97, 78.22, 76.09, 75.86, 75.75, 75.30, 74.84, 74.72, 74.20, 74.09, 73.70, 73.43, 73.30, 73.02, 72.78, 72.68, 70.89, 69.84, 68.48, 68.42, 67.30, 64.03.

O-(2,3,4,6-Tetra-O-benzyl-α-D-galactopyranosyl)-(1-4)-(2-azido-3,6-di-O-benzyl-2-deoxy-α-D-glucopyranosyl)-(1-6)-2,3,4,5-tetra-O-benzyl-1-O-(dibenzyloxyphosphoryl)-D-chiro-inositol (12)

To a solution of 11 (59 mg, 0.041 mmol) in a 1:1 mixture of dichloromethane-acetonitrile (1 mL), N,N-diisopropyl-dibenzyl phosphoramidite (30.5 mL, 0.091 mmol) and tetrazole (13.1 mg, 0.186 mmol) were added and the mixture was stirred for 1 h at room temperature The reaction mixture was cooled to 0° C. and t-butyl hydroperoxide (4.7 M isooctane solution, 90 mL) was added and stirring continued for 1 h. The solution was then evaporated to dryness and the residue was purified by column chromatography (Hex 6: AcoEt 1) to give pure 12 as a syrup (67.6 mg, 97%). $^1$H NMR (CDCl$_3$, 500 MHz): d 7.4–7.1 (m, 55H, ArH), 5.54 (d, J=3.7 Hz, 1H, H$_{1c}$), 5.02–4.44 (m, 21H, AB System), 4.87 (dd, J$_1$=4.8 Hz, J$_2$=8.4 Hz, 1H, H$_{1a}$), 4.79 (d, J=4.8 Hz, 1H, H$_{1b}$), 4.33 (d, J=12.2 Hz, 1H, AB System), 4.24 (d, J=11.7 Hz, 1H, AB System), 4.18 (d, J=8.7 Hz, 1H, AB System), 4.13 (t, J=3.8 Hz, 1H, H$_{6b}$), 4.11–4.04 (m, 3H, H$_{5b}$+H$_{4b}$+H$_{2a}$), 4.02 (dd, J$_1$=3.3 Hz, J$_2$=10.3 Hz, 1H, H$_{2c}$), 3.97 (m, 1H, H$_{4c}$), 3.91 (broad t, J=6.8 Hz, 1H, H$_{5c}$) 3.87 (m, 2H, H$_{3c}$+H$_{3b}$), 3.83 (t, J$_1$9.1 Hz, 1H, H$_{4a}$), 3.74 (t, J=9.5 Hz, 1H, H$_{3a}$) 3.71 (dd, J$_1$=3.3 Hz, J$_2$=9.7 Hz, 1H, H$_{5a}$), 3.62 (dd, J$_1$=2.4 Hz, J$_2$=11.2 Hz, 1H, H$_{6b}$), 3.49 (m, 2H, H$_{2b}$+H$_{6c}$), 3.38 (dd, J$_1$=5.3 Hz, J$_2$=8.6 Hz, 1H, H$_{6c}$), 3.28 (broad d, J=9.5 Hz, 1H, H$_{6b}$). $^{13}$C NMR (CDCl$_3$, 125 MHz): d 138.88, 138.74, 138.71, 138.57, 138.43, 138.30, 138.19, 138.15, 137.99, 137.95, 128.63, 128.58, 128.56, 128.53, 128.48, 128.44, 128.43, 128.40, 128.38, 128.36, 128.34, 128.30, 128.28, 128.25, 128.23, 128.22, 128.19, 128.18, 128.16, 128.12, 128.11, 128.09, 128.05, 128.02, 128.01, 128.00, 127.98, 127.93, 127.87, 127.80, 127.78, 127.73, 127.66, 127.63, 127.56, 127.52, 127.48, 127.46, 127.43, 127.41, 127.37, 127.34, 98.32 (anomeric C), 97.71 (anomeric C), 81.37, 81.02, 80.68, 79.00, 77.92, 77.89, 77.50, 77.26, 76.12, 75.90, 75.75, 74.85, 74.73, 74.71, 74.66, 74.30, 74.02, 73.89, 73.44, 73.08, 72.73, 72.70, 72.65, 72.62, 72.40, 71.17, 69 81, 69.59, 69.55, 69.33, 69.28, 69.26, 69.21, 68.46, 68.42, 64.10.

O-α-D-galactopyranosyl-(1-4)-2-ammonio-2-deoxy-α-D-glucopyranosyl-(1-6)-D-chiro-inositol-1-phosphate (13, RGL 1022)

To a solution of 12 (62.8 mg, 0.037 mmol) in methanol (4.3 mL) 10% Pd on C (176 mg), AcOH/AcONa buffer (0.2 M, pH 5, 4.3 mL) and THF (0.6 mL) were added. The mixture was stirred under a hydrogen atmosphere for 24 h and then filtered a lyophilised to give 13. $^1$H NMR (D$_2$O, 500 MHz): d 5.49 (broad s, 1H, H$_{1c}$), 5.12 (broad s, 1H$_{1b}$), 4.53 (m, 1H, H$_{1a}$), 4.26–3.6 (m, 17H). $^{31}$P NMR (D$_2$O, 202 MHz): d 3.38.

O-(2,3,4,6-Tetra-O-acetyl-β-D-galactopyranosyl)-(1-4)-(2-azido-3,6-di-O-benzyl-2-deoxy-α-D-glucopyranosyl)-(1-6)-1-O-allyl-2,3,4,5-tetra-O-benzyl-D-chiro-inositol (15)

To a solution of compound 14 (36.3 mg, 0.074 mmol) and compound 4 (38.8 mg, 0.041 mmol) in anhydrous ether (0.5 mL) powdered 4 Å molecular sieves were added and the mixture was stirred for 30 min at room temperature. Then TMSOTf (0.11 M solution in ether, 33 mL) was added and the mixture was stirred at room temperature for 45 min. The mixture was treated with Et$_3$N, filtered and evaporated. The residue was fractionated by column chromarography (Hexane 3: AcoEt 1) to give 15 (36.8 mg, 70%). $^1$H NMR (CDCl$_3$, 500 MHz): 7.43–7.21 (m, 30H, ArH), 5.81 (m, 1H, OCH$_2$CH=CH$_2$), 5.20 (m, 1H, OCH$_2$CH=CH), 5.19 (m, 1H), 5.14 (m, 1H, OCH$_2$CH=CHH), 5.05 (d, J=10.5 Hz, 1H, AB System), 5.02 (dd, J$_1$=10.5 Hz, J$_2$=8.1 Hz, 1H, H$_{2c}$) 4.96–4.89 (m, 3H, AB System), 4.79 (m, 2H, AB System), 4.73 (d, J=3.8 Hz, 1H, H$_{1b}$), 4.69–4.62 (m, 6H, H$_{5c}$+H$_{3c}$+H$_{6c}$+3H), 4.25 (d, J=8.2 Hz, 1H, H$_{1c}$), 4.21 (m, 1H, OCHHCH=CH$_2$), 4.18 (d, J=12.2 Hz, 1H, AB System), 4.0–3.71 (m, 12H, OCHHCH=CH$_2$+H$_{6b}$+H$_{4b}$+H$_{3a}$+H$_{5b}$+H$_{3b}$+6H), 3.47 (dd, J$_1$=3.7 Hz, J$_2$=10.1 Hz, 1H, H$_{2b}$), 3.42 (m, 2H ), 3.17 (broad d, J=10.8 Hz, 1H, H$_a$), 2.07 (s, 3H, CH$_3$COO), 1.98 (s, 3H, CH$_3$COO), 1.92 (s, 3H, CH$_3$COO), 1.69 (s, 3H, CH$_3$COO). $^{13}$C NMR (CDCl$_3$, 125 MHz): d 170.19, 170.15, 170.02, 168.94, 139.06, 138.89, 138.75, 138.70, 138.26, 137.40, 134.87, 128.71, 128.40, 128.36, 128.32, 128.20, 128.14, 127.69, 127.63, 127.56, 127.54, 127.45, 127.24, 99.85 (anomeric C), 97.75 (anomeric C), 81.94, 81.71, 80.02, 78.88, 78.17, 77.28, 77.03, 76.77, 76.11, 76.07, 75.84, 75.70, 75.20, 73.95, 73,54, 73.42, 73.26, 72.61, 70.90, 70.54, 70.40, 69.41, 66.88, 66.74, 63.16, 60.94, 60.45, 20.67, 20.62, 20.56, 20.51,.

O-(2,3,4,6-Tetra-O-benzyl-β-D-galactopyranosyl)-(1-4)-(2-azido-3,6-di-O-benzyl-2-deoxy-α-D-glucopyranosyl)-(1-6)-1-O-allyl-2,3,4,5-tetra-O-benzyl-D-chiro-inositol (16)

To a solution of 15 (32 mg, 0.025 mmol) in MeOH (0.5 mL) a 1M solution of sodium methoxide (20 mL) was added and the mixture stirred for 20 min at room temperature. Then the mixture was evaporated to dryness, toluene was added and evaporated. The residue was solved in DMF (0.5 mL) and sodium hydride (8 mg, 0.2 mmol) and benzyl bromide (18 mL, 0.15 mmol) were added. The mixture was stirred overnight at room temperature and then cooled to 0° C., methanol was added and the mixture was extracted with AcOEt. The extract was washed with saturated aqueous ammonium chloride, and saturated aqueous sodium chloride, dried over Na$_2$SO$_4$ and evaporated. The residue was purified by column chromatography (Hexanes: AcOEt 1) to give pure 16 (31.5 mg, 86%). $^1$H NMR (CDCl$_3$, 500 MHz): d 7.38–7.06 (m, 50H, ArH), 5.74 (m, 1H, OCH$_2$CH=CH$_2$), 5.15 (m, 1H, OCH$_2$CH=CHH), 5.12 (d, J=10.5 Hz, 1H, AB System), 5.10 (m, 1H, OCH$_2$CH=CHH), 4.96–4.59 (m, 14H, AB System), 4.71 (d, J=4.1 Hz, 1H, H$_{1b}$), 4.49 (m, 2H, AB System), 4.31 (d, J=12.3 Hz, 1H, AB System), 4.25 (d, J=7.7 Hz, 1H, H$_{1c}$), 4.20 (m, 2H, AB System), 4.17–4.12 (m, 2H, OCHHCH=CH$_2$+1H), 4.04 (t, J=9.0 Hz, 1H, H$_a$), 3.97 (dd, J$_1$=3.1 Hz, J$_2$=9.7 Hz, 1H, H$_a$), 3.93 (m, 1H, H$_{4b}$), 3.9 (m, 1H, OCHHCH=CH$_2$), 3.86–3.71 (m, 7H, H$_{3b}$+H$_{2c}$+4H$_a$+1H), 3.45 (t, J=8.6 Hz, 1H, H$_{4c}$), 3.42 (dd, J$_1$=3.6 Hz, J$_2$=10.3 Hz, 1H, H$_{2b}$), 3.3–3.21 (m, 4H, H$_{3c}$+H$_{5c}$+2H).

O-(2,3,4,6-Tetra-O-benzyl-β-D-galactopyranosyl)-(1-4)-(2-azido-3,6-di-O-benzyl-2-deoxy-α-D-glucopyranosyl)-(1-6)-2,3,4,5-tetra-O-benzyl-D-chiro-inositol (17)

A solution of the iridium catalyst in anhydrous THF (5.9×10$^{-3}$ M Solution, 92 mL) previously treated under a hydrogen atmosphere for 30 min was added to a solution of 16 (26.1 mg, 0.018 mmol) in anhydrous THF (0.18 mL). The mixture was stirred to room temperature for 1.5 h and cooled to 0° C. THF (1 mL), NBS (4.58 mg, 0.025 mmol) and water (60 mL) were added and the mixture was stirred at 0° C. for 20 min. Then saturated aqueous NaHCO$_3$ was added and the mixture extracted with CH$_2$Cl$_2$. The extract was washed with saturated aqueous NaCl, dried and evaporated. The residue was purified by column chromatography (Hexane 3: AcOEt 1-Hex 2: AcOEt 1) to give pure 17 (21.1 mg, 83%). $^1$H NMR (CDCl$_3$, 500 MHz): d 7.36–707 (m, 50H, ArH), 5.13 (d, J=10.1 Hz, 1H, AB System), 4.89–4.60 (m, 13H, AB System), 4.78 (d, J=3.8 Hz, 1H, H$_{1b}$), 4.48 (m, 2H, AB System), 4.32 (d, J=11.7 Hz, 1H, AB System), 4.24 (d, J=7.7 Hz, 1H, H$_{1c}$), 4.18 (m, 2H, AB System), 4.12–4.04 (m, 5H, AB System×2+H$_{5c}$+H$_{4b}$+H$_a$), 3.99 (dd, J$_1$=2.2, J$_2$=9.5 Hz, 1H, H$_a$), 3.87–3.68 (m, 8H, H$_{4c}$+H$_{3b}$+H$_{2c}$+H$_{5b}$+H$_{1a}$+H$_{6c}$+2H), 3.45 (t, J=8.6 Hz, 1H, H$_a$), 3.42 (dd, J$_1$=3.8 Hz, J$_2$=10.1 Hz, 1H, H$_{2b}$), 3.3–3.23 (m, 3H, H$_{3c}$+2H$_a$), 3.12 (broad d, J=10.2 Hz, 1H, H$_{6c}$), 1.83 (s, 1H, OH$_{1a}$). $^{13}$C NMR (CDCl$_3$, 125 MHz): d 139.07, 138.74, 138.71, 138.66, 138.57, 138.49, 138.44, 138 26, 138.14, 137.99, 128.63, 128.51, 128.42, 128.37, 128.35, 128.33, 128.29, 129.19, 128.16, 127.98, 127.93, 127.83, 127.80, 127.77, 127.76, 127.74, 127.73, 127.71, 127.67, 127.64, 127.61, 127.58, 127.52, 127.50, 127.48, 127.44, 127.39, 127.37, 127.34, 127.27, 102.66 (anomeric C), 98.40(anomeric C), 82.36, 81.69, 81.36, 80.06, 79.67, 78.26, 76.78, 76.61, 76.20, 76.01, 75.71, 75.25, 75.03, 74.75, 73.76, 73.40, 73.21, 73.13, 73.02, 72.72, 72.68, 71.09, 68.12, 67.99, 67.52, 67.36, 63.28, 25.64.

O-(2,3,4,6-Tetra-O-benzyl-β-D-galactopyranosyl)-(1-4)-(2-azido-3,6-di-O-benzyl-2-deoxy-α-D-glucopyranosyl)-(1-6)-2,3,4,5-tetra-O-benzyl-1-O-(dibenzyloxyphosphoryl)-D-chiro-inositol (18)

To a solution 17 (21 mg, 0.015 mmol) in a 1:1 mixture of CH$_2$Cl$_2$:CH$_3$CN (0.4 mL), N,N-diisopropyl dibenzyl phosphoramidite (16 mL, 0.046 mmol) and tetrazole (8 mg, 0.112 mmol) was added and the mixture was stirred for 3 h at room temperature. The reaction mixture was then cooled to 0° C. and t-butyl hydroperoxide (4.7 M isooctane solution, 34 mL) was added and stirring was continued for 1 h. The solution was then evaporated to dryness and the residue was purified by column chromatography (cyclohexane 3: AcOEt 1) to give 18 (39%). $^1$H NMR (CDCl$_3$, 500 MHz): d 7.39–7.04 (m, 60H, ArH), 5.09 (d, J=10.1 Hz, 1H, AB System), 4.97–4.44 (m, 20H, AB System), 4.88 (d, J=4.0 Hz, 1H, H$_{1a}$) 4.73 (d, J=3.8 Hz, H$_{1b}$), 4.31 (d, J=12.0 Hz, 1H, AB System), 4.27 (d, J=7.7 Hz, 1H, H$_{1c}$), 4.19 (m, 2H, AB System), 4.13–4.01 (m, 4H, H$_{2a}$+1H$_a$+2H$_b$), 3.85 (m, 1H, 1H$_c$), 3.80–3.67 (m, 6H, H$_{3b}$+H$_{2c}$+3H$_a$+1H), 3.47–3.39 (m, 2H, H$_{2b}$+1H), 3.30–3.39 (m, 2H, H$_{2b}$+1H), 3.30–3.23 (m, 3H, 1H$_c$+2H), 3.14 (m, 1H, 1H$_b$). $^{31}$P NMR (CDCl$_3$, 202 MHz): d −2.20.

O-β-D-galactopyranosyl-(1-4)-2-ammonio-2-deoxy-α-D-galactopyranosyl-(1-6)-D-chiro-inositol-1-phosphate (19)

To a solution of 18 (3.3 mg, 1.9 mmol) in methanol (0.22 mL) AcOH/AcONa buffer (0.2 M, pH5, 0.22 mL) and 10% Pd/C (5 mg) were added. The mixture was stirred under a hydrogen atmosphere for 2 h and then filtered and liophylized. The residue was passed through a sephadex G-10 column (10% EtOH in water) to give pure 19. $^1$H NMR (D$_2$O, 500 MHz). d 5.13 (broad s, 1H, H$_{1b}$), 4.56 (m, 1H, H$_{1a}$), 4.50 (d, J=7.5 Hz, 1H, H$_{1c}$), 4.24–3.57 (m, 17H). $^{31}$P NMR (D$_2$O, 202 MHz): d 3.36.

O-(3,4,6-Tri-O-benzyl-2-O-pivaloyl-α-D-mannopyranosyl)-(1-2)-(3,4,6-tri-O-benzyl-α-D-mannopyranosyl)-(1-6)-(2,3,4-tri-O-benzyl-α-D-mannopyranosyl)-(1-4)-(2-azido-3,6-di-O-benzyl-2-deoxy-α-D-glycopyranosyl)-(1-6)-1-O-allyl-2,3,4,5-tetra-O-benzyl-D-chiro-inositol (21)

To a mixture 20 (104 mg, 0.067 mmol), 14 (89.41 mg, 0.094 mmol) and 4 Å molecular sieves in CH$_2$Cl$_2$ (2 mL) at room temperature was added TMSOTf (1.0 mL, 0.005 mmol). After 1.5 h at room temperature the reaction mixture was neutralized with Et$_3$N, filtered and evaporated to dryness. The residue was purified on column chromatography (cyclohexane 10: AcOEt 1) to give 21 (62.2 mg, 58%). $^1$H NMR (CDCl$_3$, 500 MHz): d 4.41–7.06 (m, 75 H, ArH), 5.86–5.77 (m, 1H, OCH$_2$CH=CH$_2$), 5.48 (dd, J=3.1 Hz, J$_2$=2.2 Hz, 1H, H$_{2c}$), 5.26 (d, 1H, J=2.0 Hz, H$_{2d}$), 5.21–5.12 (m, 2H, OCH$_2$CH=CH$_2$), 5.01 (d, 1H, J=2.0 Hz, H$_{1c}$), 4.96–3.34 (m, 63H), 1.72 (s, 9H, $^1$Bu), O-(2,3,4,6-Tetra-O-benzyl-α-D-mannopyranosyl)-(1-2)-(3,4,6-tri-O-benzyl-α-D-mannopyranosyl)-(1-6)-(2,3,4,6-tri-O-benzyl-α-D-mannopyranosyl)-(1-4)-(2-azido-3,6-di-O-benzyl-2-deoxy-α-D-glucopyranosyl)-(1-6)-1-O-allyl-2,3,4,5-tetra-O-benzyl-D-chiro-inositol (22)

To a solution of 21 (97.3 mg, 0.042 mmol) in 1:1 methanol: THF (1.35 mL), sodium methoxide in methanol (1M solution, 94 mL) was added and the mixture was stirred overnight at room temperature. The solution was evaporated to dryness, toluene was added to the residue and evaporated. The residue was solved in DMF (1.35 mL) and NaH (3.3 mg) and benzyl bromide (7.5 mL) were added. The mixture was stirred at room temperature for 24 h, cooled to 0° C., treated with MeOH and extracted with CH$_2$Cl$_2$. The extract was washed with sat. NH$_4$Cl, sat. NaCl, dried over Na$_2$SO$_4$ and evaporated. The residue was purified by column chromatography (Hexane 6: AcoEt 1) to give pure 22 (99%). $^1$H NMR (CDCl$_3$, 500 MHz): d 7.38–7.09 (m, 80H, ArH), 5.82 (m, 1H, OCH$_2$CH=CH$_2$), 5.28 (d, J=2.1 Hz, 1H, H$_{1d}$), 5.23–5.12 (m, 3H, OCH$_2$CH=CH$_2$+1H$_d$), 4.98–4.76 (m, 9H, AB System), 4.90 (m, 1H, 1H$_d$), 4.70 (d, J=3.6 Hz, 1H, 1H$_b$), 4.70–3.35 (m, 55H).

O-(2,3,4,6-Tetra-O-benzyl-α-D-mannopyranosyl)-(1-2)-(3,4,6-tri-O-benzyl-α-D-mannopyranosyl)-(1-6)-(2,3,4-tri-O-benzyl-α-D-mannopyranosyl)-(1-4)-(2-azido-3,6-di-O-benzyl-2-deoxy-α-D-glucopyranosyl)-2,3,4,5-tetra-O-benzyl-D-chiro-inositol (23)

A solution of the iridium catalyst in anhydrous THF (5.9×10$^{-3}$ M, solution, 88 mL) previously treated under a hydrogen atmosphere for 30 min was added over a solution of 22 (40 mg, 0.071 mmol) in THF (0.2 mL). The mixture was stirred for 45 min and THF (1 mL), NBS (4.38 mg, 0025 mmol) and water (60 mL) were added and the mixture was stirred for 5 min, treated with saturated NaHCO$_3$, and extracted with CH$_2$Cl$_2$. The extract was dried over Na$_2$SO$_4$ and evaporated. The residue was purified by column chromatography (Hexane 4: AcOEt 1-Hexane 2: AcOEt 1) to give 23 (93%). $^1$H NMR (CDCl$_3$, 500 MHz):d 7.35–7.06 (m, 80H, ArH), 5.26 (d, J=2.2 Hz, 1H, 1H$_d$), 5.11 (d, J=2.0 Hz, 1H 1H$_d$), 4.95 (m, 1H, AB System), 4.86 (d, J=2.0 Hz, 1H, 1H$_d$), 4.89–3.2 (m, 62H).

O-(2,3,4,6-Tetra-O-benzyl-α-D-mannopyranosyl)-(1-2)-(3,4,6-tri-O-benzyl-α-D-mannopyranosyl)-(1-6)-(2,3,4-tri-O-benzyl-α-D-mannopyranosyl)-(1-4)-(2-azido-3,6-di-O-benzyl-2-deoxy-α-D-glucopyranosyl)-2,3,4,5-tetra-O-benzyl-1-O-(dibenzylphosphoryl)-D-chiro-inositol (24)

To a solution of 23 (12.8 mg, 0.005 mmol) in a 1:1.5 mixture of $CH_2Cl_2$:$CH_3Cl$ (1.6 mL), N,N-diisopropyl dibenzyl phospharamidite (22 mL, 0.067 mmol) and tetrazole (5.7 mg, 0.080 mmol) was added and the mixture stirred for 45 min at room temperature. The mixture was cooled to 0° C. and t-butyl hydroperoxide (4.7M isooctane solution, 50 ml) was added and stirring was continued for 30 min. The mixture was evaporated to dryness and the residue was purified by column chromatography (Hexane 1: Ether 2) to give 24 (60%). $^1H$ NMR ($CDCl_3$, 500 MHz): d 7.40 (m, 90H, ArH), 5.27 (d, J=2.3 Hz, 1H, $1H_a$), 5.11 (d, J=2.0 Hz, 1H, $1H_d$), 4.96–3.26 (m, 68H).

O-α-D-Mannopyranosyl-(1-2)-O-α-D-mannopyranosyl-(1-6)-O-α-D-mannopyranosyl-(1-4)-O-2ammonio-2-deoxy-α-D-glucopyranosyl-(1-6)-D-chiro-inositol-1-phosphate (25)

A solution of 24 (3 mg) in THF-EtOH (1:11) (50 mL) containing $NH_4OAc$ (0.5 mg) was stirred for 12 h under atmospheric pressure of $H_2$ with 10% Pd/C, the filtered over Celite and concentrated. The crude mixture was passed through Sephadex G.25 eluting with $H_2$-EtOH (10:1). Liophylisation gave 25 as a white powder. $^1H$ NMR ($CDCl_3$, 500 MHz): d 5.26 (bs, 1H), 5.17 (bs, 1H), 5.06 (bs, 1H), 4.8 (bs, 1H), 452–3.54 (m, 29H), 2.97 (bs, 1H).

(O-α-D-Galactopyranosyl-(1-4)-(2-amino-2-deoxy-α-D-glucopyranosyl)-(1-6)-D-myo-inositol) (28, RGL 1014).

To a mixture of compound 1 (114 mg, 1 equiv.), 2,3,4,6-tetra-O-benzyl-D-galactopyranosyl trichloroacetimidate (210 mg) and 4 Å molecular sieves in $CH_2Cl_2$ (20 mL) at room temperature was added TMSOTf (1.6 mL, 0.008 mmol). After 1 h, the reaction mixture was neutralised with solid $NaHCO_3$, filtered over Celite and evaporated. The crude mixture was purified by flash chromatography to give a pure fully protected trisaccharide (210 mg). To a solution of this fully protected trisaccharide (149 mg) in wet chloroform (3 mL), trifluoroacetic acid (0.4 mL) was added and the mixture was kept for 18 h at room temperature. Saturated aqueous $NaHCO_3$ was then added at 0° C., the aqueous layer extracted with $CH_2Cl_2$ (3×10 mL) and the combined organic extracts were dried and concentrated. The residue was purified by column chromatography (EtOAc: hexane 1:25) to afford a colourless oil that was dissolved in EtOH (1.8 mL) containing 10% Pd/C. The reaction mixture was stirred for 18 h under atmospheric pressure of hydrogen, filtered over Celite and concentrated. The crude product was purified through a Sephadex G-25 column and liophylised to give pure 2. $^1H$-RMN ($D_2O$, 500 MHz): 539 (1 H, d, J=3.4, Gal H-1); 5.19 (1 H, d, J=3.6, GlcN H-1); 3.98 (1 H, t, J=2.75, Ins H-2); 3.97 (1 H, ddd, J=10.3, 3.4, 2.8, GlcN H-5); 394 (1 H, m, Gal H-5); 3.92 (1 H, m, Gal H-4); 3.84 (1 H, dd, J=10.6, 8.9, GlcN H-3); 3.81 (2 H, m, GlcN H-6); 3.79 (1 H, m, Gal H-2); 3.77 (1 H, m, Gal H-3); 3.7 (1 H, m, Ins H-1); 3.67 (2 H, m, Gal H-6); 3.66 (1 H, m, Ins H-6); 3.62 (1 H, dd, J=8.9, 10.3, GlcN H-4); 3.61 (1 H, dd, J=9.7, 10.2, Ins H-4); 3.48 (1 H, dd, J=10.2, 2.9, Ins H-3); 3.32 (1 H, dd, J=8.9, 9.7, Ins H-5); 2.78 (1 H, dd, J=3.6, 10.6, GlcN H-2). $^{13}C$-NMR ($D_2O$, 125.7 MHz) 100.4 (GlcN C-1), 100.2 (Gal C-1), 80.9 (Ins C-6), 77.5 (GlcN C-4), 74.5 (GlcN C-3), 73.4 (Ins C-5), 72.8 (Ins C-2), 72.8 (Ins C-4), 72.1 (Gal C-5), 71.9 (Ins C-1), 71.3 (Ins C-3), 71.1 (GlcN C-5), 69.7 (Gal C-3), 69.5 (Gal C-4), 69.0 (Gal C-2), 61.5 (Gal C-6), 60.8 (GlcN C-6), 55.4 (GlcN C-2).

Synthesis of RGL1105

1"-D-4'-O-(2",3",4"-tri-O-benzyl-6"-tertbutyldimethylsilyl-α-D-mannopyranosyl)-[1'-D-6-O-(2'-azido-3',6'-di-O-benzyl-2'-deoxy-α-D-glucopyranosyl)-1,2-O-(L-1,7,7-trimethyl[2.2.1]-bicyclohept-2-ylidene)-3,4,5-tri-O-benzyl-myo-inositol](3)

O-benzyl-myo-inositol](3)

A mixture of compounds 1 (284 mg, 0.298 mmol) and 2 (340 mg, 0.408 mmol), was dissolved in Toluene and the solvent removed (3×10 mL). To the water-free solid mixture, $Et_2O$ anh. (10 mL) and 4 Å powdered molecular sieves was added and allowed to dissolve at room temperature under Argon atmosphere. After 5 min, TMSOTf (12 μL, 0.066 mmol) was added and the reaction allowed to proceed for 90 min. Then, the reaction was quenched with $Et_3N$ (2 mL) and after 5 min stirring, the solvents are removed and the residue purified by column chromatography ($SiO_2$, hexane/AcOEt 19:1), to obtain 3 (363 mg, 75%). $^1H$ NMR ($CDCl_3$, 500 MHz): d 7.72–7.58 (m, 5H, ArH), 7.42–7.13 (m, 39H, ArH), 7.07 (m, 5H, ArH), 6.94 (t, J=7.5 Hz, 1H, ArH), 5.58 (d, J=3.0 Hz, 1H, H anom.), 5.261 (d, J=2.9 Hz, 1H, H anom.), 4.95 (d, J=11 Hz, 1H, H benc.), 4.87 (d, J=11 Hz, 1H, H benc.), 4.75–4.63 (m, 7H), 4.62–4.49 (m, 4H), 4.42 (m, 2H), 4.46 (m, 3H), 4,7 (d, J=12.0 Hz, 1H, H benc.), 4.12 (m, 3H), 4.1 (dd, $J_1$=3 Hz, $J_2$=11.5 Hz, 1H), 3.98–3.91 (m, 3H), 3.78–3.89 (m, 4H), 3.69 (m, 1H), 3.49–3.61 (m, 2H), 3.44 (m, 1 H), 1.99 (m, 2H), 1.74–1.85 (m, 2H), 1.55 (d, J=12.5 Hz, 1H),1.47 (m, 1H), 1.27–1.38 (m, 1H), 1.10 (s, 3H), 095 (s, 3H), 0.92 (s, 3H).

1"-D-4'-O-(2",3",4"-tri-O-benzyl-α-D-mannopyranosyl)-[1'-D-6-O-(2'-azido-3',6'-di-O-benzyl-2'-deoxy-α-D-glucopyranosyl)-1,2-O-(L-1,7,7-trimethyl[2.2.1]-bicyclohept-2-ylidene)-3,4,5-tri-O-benzyl-myo-inositol](4)

A solution of 3 (290 mg, 0.179 mmol) in THF (15 mL) under Argon atmosphere, was treated with TBAF (1.0 M in THF, 1.8 mL, 1.800 mmol) at 0° C. The reaction mixture was allowed to reach room temperature and kept stirring for 66 h. Then, the solvents were removed, the remaining material redissolved in AcOEt (50 mL), washed with NaCl s.s. (3×50 mL), dried over $MgSO_4$ and the solvents evaporated. The residue was purified by column chromatography ($SiO_2$, hexane/AcOEt 9:1 to 8:1 to 6:1 and finally 4:1), to obtain 4 (206 mg, 83%). $^1H$ NMR ($CDCl_3$, 500 MHz): 7.25–7.44 (m, 37H, ArH), 7.11–7.20 (m, 3H, ArH), 5.68 (d, J=3.5 Hz, 1H, H anom.), 5.32 (d, J=2 Hz, 1M, H anom.), 4.95 (m, 1H), 4.55–4.86 (m, 12H), 4.50 (d, J=12 Hz, 1H, H benc.), 4.40 (d, J=12 Hz, 1H, H benc.),4.34 (m, 1H), 4.20 (d, J=12 Hz, 1H, H benc.), 4.10 (m, 3H), 3.82–4.03 (m, 6H), 3.64–3.76 (m, 5H), 3.47–3.58 (m, 2H), 3.41 (dd, $J_1$=3.5 Hz, $J_2$=10 Hz, 1H), 2.4 (s,1H, OH), 1.97 (m, 2H), 1.74–1.84 (m, 2H), 1.53 (d, J=13 Hz, 1H), 1.47 (m, 1H), 1.24–1.35 (m, 1H), 1.13 (s, 3H), 0.94 (s, 3H), 0.93 (s, 3H).

1"-D-4'-O-(2",3",4"-tri-O-benzyl-6"-dibenzylphosphate-α-D-mannopyranosyl)-[1'-D-6-O-(2'-azido-3',6'-di-O-benzyl-2'-deoxy-α-D-glucopyranosyl)-1,2-O-(L-1,7,7-trimethyl[2.2.1]-bicyclohept-2-ylidene)-3,4,5-tri-O-benzyl-myo-inositol] (5)

To a solution of trisaccharide 4 (190 mg, 0.137 mmol) and 1H-Tetrazole in anhydrous $CH_2Cl_2$ (10 mL) under Argon atmosphere and at 0° C., dibenzyl diisipropylphosphoramidite (DBPA, 0.1 mL, 0.298 mmol) was added. The reaction mixture was stirred for 3 h, while allowing to reach room temperature. Then, the reaction mixture was cooled to 0° C. and a solution of 70% 3-chloroperbenzoic acid (85 mg, 0.345 mmol) in anh. $CH_2Cl_2$ (5 mL) was added. The mixture was stirred for 1 h, diluted with $CH_2Cl_2$ (25 mL), washed with sat. $Na_2SO_3$ (2×50 mL), sat. $NaHCO_3$ (2×50 mL) and sat. NaCl (2×50 mL), dried over $MgSO_4$ and concentrated. Flash chromatography of the crude mixture (hexane/AcOEt 9/1, 8/1, 7/1, 6/1, 5/1 and 4/1) gave compound 5 (210 mg, 93%). $^1$H-NMR ($CDCl_3$, 500 MHz): d 7.13–7.42 (m, 49H, ArH), 7.08 (m, 1H, ArH), 5.66 (d, J=3.5 Hz, 1H, H anom.), 5.28 (d, J=2 Hz, 1H, H anom.), 4.90–5.03 (m, 6H), 4.75–4.81 (m, 4H), 4.72 (d, J=12 Hz, 1H, H benc.), 4.65 (m, 2H), 4.52–4.61 (m, 3H), 4.45 (m, 2H), 4.34 (m, 2H), 4.15–4.29 (m, 3H), 4.03–4.12 (m, 4H), 3.80–3.94 (m, 5H), 3.72 (m, 2H), 3.56 (m, 2H), 3.49 (m, 1H), 3.57 (dd, $J_1$=3.5 Hz, $J_2$=10 Hz, 1H), 1.97 (m, 2H), 1.78 (m, 2H), 1.52 (d, J=12.5 Hz, 1H), 1.46 (m, 1H), 1.28 (m, 1H), 1.12 (s, 3H), 0.93 (s, 3H), 0.89 (s, 3H). $^{31}$P-NMR ($CDCl_3$, 202 MHz) d –1.72.

1"-D-4'-O-(2",3",4"-tri-O-benzyl-6"-dibenzylphosphate-α-D-mannopyranosyl)-[1'-D-6-O-(2'-azido-3',6'-di-O-benzyl-2'-deoxy-α-D-glucopyranosyl)-3,4,5-tri-O-benzyl-myo-inositol](6)

To a solution of trisaccharide 5 (200 mg, 0.122 mmol) in $CH_2Cl_2$ (15 mL) $H_2O$ (0.2 mL, 11.1 mmol), and trifluoroacetic acid (0.6 mL, 7.81 mmol) were added and the reaction stirred for 18 h at r.t. The mixture was then diluted with AcOEt (50 mL), washed with sat. $NaHCO_3$ (2×50 mL), sat. NaCl (3×50 mL), dried over $MgSO_4$ and concentrated. Flash chromatography of the crude mixture (hexane/AcOEt 4/1, 2/1, 1/1 y 1/2) gave compound 6 (142 mg, 77%). $^1$H-NMR ($CDCl_3$, 500 MHz): d 7.10–7.39 (m, 50H), 5.53 (d, J=3.5 Hz, 1H, H anom.), 5.24 (d, J=2.5 Hz, 1H, H anom.), 4.87–5.03 (m, 8H), 4.72–4.79 (m, 4H), 4.63 (m, 2H), 4.57 (d, J=12Hz, 1H, H benc.), 4.49 (d, J=12 Hz, 1H, H benc.), 4.25–4.38 (m, 3H), 4.09–4.26 (m, 4H), 4.01–4.09 (m, 3H), 3.95 (m, 1H), 3.84 (m, 3H), 3.69 (m, 3H), 3.6 (m, 1H), 3.5 (m, 1H), 3.43 (m, 2H), 3.37 (m, 1H), 3.29 (m, 1H), 2.94 (wide s., 1H, OH). $^{31}$P-RMN ($CDCl_3$, 202 MHz): d –1.79.

1"-D-4'-O-(6"-phosphate-α-D-mannopyranosyl)-[1'-D-6-O-(2'-amino-2'-deoxy-α-D-glucopyrarosyl)-myo-inositol] (RGL 1105)

To a suspension of trisaccharide 6 (115 mg, 0.076 mmol) in a mixture of $MeOH/H_2O$ (5 mL, 9:1) 10% Pd/C (162 mg, 0.152 mmol) was added and the reaction stirred under hydrogen atmosphere at r.t. for 24 h. The solvent was evaporated, the crude suspended in $H_2O$ (10 mL), filtered through celite and the filtrate lyophilized to give RGL1105 (45 mg, quant.). $^1$H-RMN ($D_2O$, 500 MHz): d 5.46 (d, 3.5 Hz, 1H, H anom.), 5.31 (s, 1H, H anom.), 4.0–4.27 (m, 6H), 3.72–3.92 (m, 8H), 3.68 (t, J=9.5 Hz, 1H), 3.54 (m, 1H), 3.41 (m, 1H). $^{31}$P-RMN ($D_2O$, 202 MHz): d 0.66.

| Assay Data | |
|---|---|
| PDH activation at 100 μM | |
| RGL1021 | 14% |
| PKA inhibition at 0.1 μM | |
| RGL1014 | 2% |
| RGL1022 | 47% |

REFERENCES:

The references mentioned herein are all expressly incorporated by reference.

[1](a) Varela-Nieto et al, *Comp. Biochem. Physiol.*, 115B:223–241, 1996; (b) Strälfors, *Bioassays*, 19:327–335, 1997; (c) Field, *Glycobiology*, 7:161–168, 1997; d) Jones & Varela-Nicto, *Int. J. Biochem. Cell Biol.*, 30:313–326, 1998.

[2] Mato et al, *Biochem. Biophys. Res. Commun.*, 146:746–770, 1987.

[3] Larner et al, *Biochem. Biophys. Res. Commnun.*, 151:1416–1426, 1998.

[4] Caro et al, *Biochem Mol. Med.* 61:214–228, 1997.

[5] For recent reviews on the synthesis of these structures see: a) Gigg & Gigg in *Glycopeptides and Related Compounds*, Large & Warren, Eds., Marcel Dekker, New York, 1997, pp 327–392; Khiar & Martin-Lomas in *Carbohydrate Mimics*. Concepts and Methods, Chapleur Ed Wiley VCH, 1998, pp 443–462; Dietrich et al, *Chem. Eur. J;*, 5:320–336, 1999.

[6] Jaramillo et al, *J. Org. Chem.*, 59, 3135–3141, 1994.

[7] Corey & Venkateswarlu, *J. Am. Chem. Soc.*, 94:6190, 1974.

[8] Ley et al, *Angew.Chem. Int. Ed. Engl.,*33:2290–2292, 1994.

[9] Kinzi & Schmidt, *Liebigs Ann. Chem*, 1537–1545, 1985.

[10] Vasella et al, *Helv. Chim. Acta.*, 74:2073–2077, 1991.

[11] Schmidt & Kinzi, *Adv. Carbohydy. Chem. Biochem.*, 50:21–123, 1994.

[12] Once et al, *Chem. Eur. J.*, 3:431–440, 1997.

[13] Rademacher et al, *Brazilian J. Med. Biol. Res.*, 27:327–341, 1994.

[14] Caro et al. *Biochem. Molec. Med.*, 61:214–228, 1997.

[15] Kunjara et al, In: Biopolymers and Bioproducts: Structure, Function and Applications, Ed Svati et al, 301–305, 1995.

[16] Zapata et al, *Carbohydrate Res.*, 264:21–31, 1994.

[17] Dietrich et al, Chem. Eur. J., 5:320–336, 1999.

[18] Baeschlin et al, Chem. Eur. J., 6(1):172–186, 2000.

WO98/11116 and WO98/11117 (Rademacher Group Limited).

WO98/11435 and WO98/10791 (Rademacher Group Limited).

WO99/38516 (Rademacher Group Limited).

What is claimed is:

1. A compound represented by the formula:

Y—X—1,6-chiro-inositol wherein:

X represents a sugar radical;

Y represents one to three sugar radicals;

the sugar residue is unsubstituted or substituted with between one and four groups, and the chiro-inositol is unsubstituted or is further substituted with between one and four groups, the group or groups being independently selected from:
(a) the phosphoryl groups phosphate, —O—P(O)(OH)$_2$, thiophosphate, —O—P(S)(OH)$_2$, phosphate esters, —O—P(O)(OH)$_2$, thiophosphate esters, —O—P(S)(OR)$_2$, phosphonate, —O—P(O)OHR, thiophosphonate, —O—P(S)OHR, substituted phosphonate, —O—P(O)OR$_1$R$_2$, substituted thiophosphonate, —O—P(S)OR$_1$R$_2$, —O—P(S)(OH)(SH) and cyclic phosphate;
(b) the phosphorus-containing groups phosphoramidite, —O—P(OR)—NR$_1$R$_2$ and phosphoramidate, —O—P(O)(OR)—NR$_1$R$_2$;
(c) the sulphur-containing groups —O—S(O)(OH), —SH, —SR, —S(—O)—R, —S(O)$_2$R, RO—S(O)$_2^-$, —O—SO$_2$NH$_2$, —O—SO$_2$R$_1$R$_2$ or sulphamide —NHSO$_2$NH$_2$;
(d) the amino groups —NHR, —NR$_1$R$_2$, —NHA$_c$, —NHCOR, —NH—O—COR, —NHSO$_3^-$, —NHSO$_2$R, —N(SO$_2$R)$_2$; the amidino group, —NH—C(=NH)NH$_2$; and the ureido groups, —NH—CO—NR$_1$R$_2$ or thiouriedo group, —NH—C(S)—NH$_2$;
(e) the hydroxy group; the substituted hydroxy groups —OR$_3$, where R$_3$ is C$_{1-10}$ unsubstituted or substituted alkyl, alkoxyalkyl, aryloxyalkyl, cycloalkyl, alkenyl (unsubstituted alkyl), alkylene (C$_{3-7}$ cycloalkyl), —OCOR, aryl, heteroaryl, acetal, or said substituted groups comprise two hydroxyl groups that are joined to form a ketal;
(f) the halogen substituents fluorine or chlorine; and
(g) hydrogen, forming a deoxy sugar; wherein R, R$_1$ and R$_2$ are independently hydrogen or C$_{1-10}$ unsubstituted or substituted alkyl or aryl, or derivatives thereof, said derivatives comprising physiologically tolerated salts, coordination complexes with metal ions, esters, free acids or bases, hydrates, prodrugs, or coupling partners selected from the group consisting of a reporter molecule, a substrate, a transport molecule, an effector, a drug, an antibody or an inhibitor.

2. The compound of claim 1 wherein the sugar reside and chiro-inositol moiety are α1,6 linked or β1,6 linked.

3. The compound of claim 1 wherein the sugar reside is an unsubstituted or substituted hexose or pentose.

4. The compound of claim 3, wherein the sugar residue is a hexose selected from the group consisting of glucose, galactose or mannose.

5. The compound of claim 3, wherein the sugar residue is a hexosamine.

6. The compound of claim 5, wherein the hexosamine is galactosamine or glucosamine.

7. The compound of claim 1 wherein the chiro-inositol is a D or L-enantionmer.

8. A compound selected from the group consisting of:

RGL1014 O-(D-galactopyranosyl)-α(1,4)-O-(2'-amino-2'-deoxy-D-glucanopyranosyl) -α(1,6)-myo-inositol;
RGL1021 O-(D-galactopyranosyl)-α(1,4)-O-(2'-amino-2'-deoxy-D-glucanopyranosyl) -α(1,6)-chiro-inositol;
RGL1022 O-(D-galactopyranosyl)-α(1,4)-O-(2'-amino-2'-deoxy-D-glucanopyranosyl) -α(1,6)-chiro-inositol-1-phosphate;
RGL1105 1"-D-4'-O-(6"-phosphate-α-D-mannopyranosyl)-[1'-D-6-O-(2'-amino-2'-deoxy-α-D-glucopyranosyl)-myo-inositol];
Compound 25 O-α-D-Mannopyranosyl-(1,2)-O-α-D-mannopyranosyl-1,6)-O-α-D-mannopyranosyl-(1,4)-O-2 ammonio-2-deoxy-α-D-glucopyranosyl(1,6-)-D-chiro-inositol-1-phosphate; and
Compound 19 O-β-D-galactopyranosyl-(1,4)-2-ammonio-2-deoxy-α-D-galactopyranosyl-(1,6)-D-chiro-inositol-1-phosphate;

and substituted forms of said compounds wherein at least one of the sugar residues and the inositol moiety are substituted with between one and four substituent groups, said substituent groups being independently selected from those consisting of:
(a) the phosphoryl groups phosphate, —O—P(O)(OH)$_2$, thiophosphate, —O—P(S)(OH)$_2$, phosphate esters, —O—P(O)(OR)$_2$, thiophosphate esters, —O—P(S)(OR)$_2$, phosphonate, —O—P(O)OHR, thiophosphonate, —O—P(S)OHR, substituted phosphonate, —O—P(O)OR$_1$R$_2$, substituted thiophosphonate, —O—P(S)OR$_1$R$_2$; —O—P(S)(OH)(SH) and cyclic phosphate;
(b) the phosphorus-containing groups phosphoramidite, —O—P(OR)—NR$_1$R$_2$ and phosphoramidate, —O—P(O)(OR)—NR$_1$R$_2$;
(c) the sulphur-containing groups, —O—S(O)(OH), —SH, —SR, —S(—O)—R, —S(O)$_2$R, RO—S(O)$_2^-$, —O—SO$_2$NH$_2$, —O—SO$_2$R$_1$R$_2$ or sulphamide, —NHSO$_2$NH$_2$;
(d) the amino groups —NHR, —NR$_1$R$_2$, —NHA$_c$, —NHCOR, —NH—O—COR, —NHSO$_3^-$, —NHSO$_2$R, —N(SO$_2$R)$_2$; the amidino group, —NH—C(=NH)NH$_2$; and the ureido groups, —NH—CO—NR$_1$R$_2$ or thiouriedo group, —NH—C(S)—NH$_2$;
(e) the hydroxy group; the substituted hydroxy groups —OR$_3$, where R$_3$ is C$_{1-10}$ unsubstituted or substituted alkyl, alkoxyalkyl, aryloxyalkyl, cycloalkyl, alkenyl (unsubstituted alkyl), alkylene (C$_{3-7}$ cycloalkyl), —OCOR, aryl, heteroaryl, acetal, or said substituted groups comprise two hydroxyl groups that are joined to form a ketal;
(f) the halogen substituents fluorine or chlorine; and
(g) hydrogen, forming a deoxy sugar; wherein R, R$_1$ and R$_2$ are independently hydrogen or C$_{1-10}$ unsubstituted or substituted alkyl or aryl, or a derivative thereof, said derivative comprising physiologically tolerated salts, coordination complexes with metal ions, esters, free acids or bases, hydrates, prodrugs, or coupling partners selected from the group consisting of a reporter molecule, a substrate, a transport molecule, an effector, a drug, an antibody or an inhibitor.

9. A composition comprising a compound of claim 1 in combination with a pharmaceutically acceptable carrier.

10. A composition comprising a compound of claim 8 in combination with a pharmaceutically acceptable carrier.

11. A method of treating a condition in a mammal ameliorated by an inositol phosphoglycan (IPG) second messenger or an IPG antagonist, the method comprising administering to the mammal a therapeutically effective amount of a compound of claim 1.

12. A method of treating a condition in a mammal ameliorated by an inositol phosphoglycan (IPG) second messenger or an IPG antagonist, the method comprising administering to the mammal a therapeutically effective amount of a compound of claim 8.

13. A compound of claim 8, wherein said substituted hydroxy group is OR$_3$, and R$_3$ is selected from the group consisting of CHF$_2$ and CF$_3$.

14. The compound of claim 8, wherein said derivative is a coordination complex with a metal ion selected from the group consisting of $M_n(+2)$ and $Z_n(+2)$.

15. The compound of claim 8, wherein said derivative is a glycolipid derivatized prodrug.

16. A compound of claim 1, wherein said substituted hydroxy group is $OR_3$, and $R_3$ is selected from the group consisting of $CHF_2$ and $CF_3$.

17. The compound of claim 1, wherein said derivative is a coordination complex with a metal ion selected from the group consisting of $M_n(+2)$ and $Z_n(+2)$.

18. The compound of claim 1, wherein said derivative is a glycolipid derivatized prodrug.

* * * * *